(12) United States Patent
LaConte et al.

(10) Patent No.: US 11,382,657 B2
(45) Date of Patent: Jul. 12, 2022

(54) SURGICAL DEVICES WITH TRIGGERED PROPULSION SYSTEM FOR INSERTING A TROCAR-CANNULA ASSEMBLY

(71) Applicant: Synergetics USA, Inc., O'Fallon, MO (US)

(72) Inventors: Matthew Paul LaConte, Chesterfield, MO (US); James C. Easley, Cottleville, MO (US); Jason Stroisch, Wentzville, MO (US)

(73) Assignee: Synergetics USA, Inc., O'Fallon, MO (US)

( * ) Notice: Subject to any disclaimer, the term of this patent is extended or adjusted under 35 U.S.C. 154(b) by 384 days.

(21) Appl. No.: 15/999,364

(22) PCT Filed: Feb. 17, 2017

(86) PCT No.: PCT/US2017/018363
§ 371 (c)(1),
(2) Date: Aug. 17, 2018

(87) PCT Pub. No.: WO2017/143184
PCT Pub. Date: Aug. 24, 2017

(65) Prior Publication Data
US 2019/0083129 A1 Mar. 21, 2019

Related U.S. Application Data

(63) Continuation-in-part of application No. 15/047,404, filed on Feb. 18, 2016, now Pat. No. 10,485,577.
(Continued)

(51) Int. Cl.
*A61B 17/34* (2006.01)
*A61B 90/00* (2016.01)
(Continued)

(52) U.S. Cl.
CPC ...... *A61B 17/3421* (2013.01); *A61B 17/3403* (2013.01); *A61B 90/03* (2016.02);
(Continued)

(58) Field of Classification Search
CPC .. A61F 9/0017; A61F 9/0026; A61F 9/00736; A61F 9/00745; A61F 9/00754;
(Continued)

(56) References Cited

U.S. PATENT DOCUMENTS 3,888,258 A * 6/1975 Akiyama .............. A61F 11/002
606/109
4,534,348 A 8/1985 Fedorov et al.
(Continued)

FOREIGN PATENT DOCUMENTS

JP 2009-072221 A 4/2009
JP 5568016 B2 8/2014
(Continued)

OTHER PUBLICATIONS

International Search Report and Written Opinion of the International Searching Authority regarding PCT/US2017/018363 dated Jul. 3, 2017; pp. 1-21.

*Primary Examiner* — Martin T Ton
(74) *Attorney, Agent, or Firm* — Armstrong Teasdale LLP

(57) ABSTRACT

Surgical devices and methods of using the surgical devices are disclosed. The surgical devices generally include a trocar, a cannula releasably mounted on the trocar, and a propulsion system operatively connected to the trocar. The cannula includes a hub, and has a central opening through which the trocar extends. The propulsion system is operable to drive the trocar axially in a forward direction away from a proximal end of the surgical device.

20 Claims, 15 Drawing Sheets

Related U.S. Application Data

(60) Provisional application No. 62/345,330, filed on Jun. 3, 2016.

(51) Int. Cl.
*A61F 9/007* (2006.01)
*A61B 17/00* (2006.01)

(52) U.S. Cl.
CPC ...... *A61F 9/00736* (2013.01); *A61B 17/3462* (2013.01); *A61B 2017/00022* (2013.01); *A61B 2017/00398* (2013.01); *A61B 2017/00477* (2013.01); *A61B 2017/00738* (2013.01); *A61B 2017/3407* (2013.01); *A61B 2017/3409* (2013.01); *A61B 2090/034* (2016.02)

(58) Field of Classification Search
CPC .. A61F 9/00763; A61F 9/00772; A61F 9/013; A61F 9/0133; A61B 17/34; A61B 17/3403; A61B 17/3405; A61B 17/3407; A61B 17/3409; A61B 17/3421; A61B 17/3494; A61B 2017/00398; A61B 2017/3405; A61B 2017/3407; A61B 2017/3409; A61M 5/3287; A61M 5/427; A61M 5/46; A61M 2005/3289
See application file for complete search history.

(56) References Cited

U.S. PATENT DOCUMENTS

| | | | |
|---|---|---|---|
| 4,834,727 A | 5/1989 | Cope | |
| 4,960,407 A | 10/1990 | Cope | |
| 5,014,717 A | 5/1991 | Lohrmann | |
| 5,242,427 A | 9/1993 | Bilweis | |
| 5,281,197 A | 1/1994 | Arias et al. | |
| 5,411,511 A | 5/1995 | Hall | |
| 5,611,805 A | 3/1997 | Hall | |
| 5,681,323 A * | 10/1997 | Arick | A61B 17/3415 606/108 |
| 6,527,780 B1 | 3/2003 | Wallace et al. | |
| 7,143,926 B2 | 12/2006 | Shelton, IV et al. | |
| 7,364,061 B2 | 4/2008 | Swayze et al. | |
| 7,431,710 B2 | 10/2008 | Tu et al. | |
| 8,287,494 B2 | 10/2012 | Ma | |
| 8,702,742 B2 | 4/2014 | Hanlon et al. | |
| 9,033,952 B2 | 5/2015 | Chen | |
| 9,072,508 B2 | 7/2015 | Callede et al. | |
| 9,113,856 B2 | 8/2015 | Callede et al. | |
| 9,173,775 B2 | 11/2015 | Haffner et al. | |
| 10,172,604 B2 | 1/2019 | Hanlon et al. | |
| 10,945,760 B2 | 3/2021 | Amon | |
| 2001/0008961 A1 | 7/2001 | Hecker | |
| 2006/0089526 A1 | 4/2006 | Chen et al. | |
| 2006/0089607 A1 | 4/2006 | Chen et al. | |
| 2010/0331858 A1* | 12/2010 | Simaan | A61B 34/37 606/130 |
| 2011/0152774 A1 | 6/2011 | Lopez et al. | |
| 2012/0271197 A1 | 10/2012 | Castle et al. | |
| 2014/0180013 A1* | 6/2014 | Hanlon | A61B 17/3415 600/201 |
| 2015/0038893 A1 | 2/2015 | Haffner et al. | |
| 2015/0094751 A1 | 4/2015 | Chen | |
| 2015/0150642 A1 | 6/2015 | Lau et al. | |
| 2015/0351960 A1 | 12/2015 | Copper | |
| 2016/0015563 A1* | 1/2016 | Humayun | A61F 9/00736 606/108 |

FOREIGN PATENT DOCUMENTS

| | | |
|---|---|---|
| WO | 0007530 A2 | 2/2000 |
| WO | 2008084063 A1 | 7/2008 |
| WO | 2016010810 A2 | 1/2016 |

\* cited by examiner

SURGICAL DEVICES WITH TRIGGERED PROPULSION SYSTEM FOR INSERTING A TROCAR-CANNULA ASSEMBLY

CROSS-REFERENCE TO RELATED APPLICATIONS

This application claims priority to U.S. Non-Provisional patent application Ser. No. 15/047,404, filed Feb. 18, 2016, and U.S. Provisional Patent Application Ser. No. 62/345,330, filed Jun. 3, 2016, the disclosures of which are hereby incorporated by reference in their entirety.

FIELD

The field of the disclosure relates generally to a surgical device including a trocar-cannula assembly and, more particularly, to surgical devices including a triggered actuation or propulsion system for precisely inserting the trocar-cannula assembly.

BACKGROUND

In ophthalmic procedures, such as vitrectomies, membranectomies, and photocoagulation, incisions are made in the eye to provide access to the posterior chamber of the eye. Typically, cannulas are inserted into these incisions to keep the incision from closing. Other surgical implements may then be inserted through the cannula into the patient's body after removal of the trocar.

Several studies have been performed to evaluate the success of methods used to gain access to the posterior chamber of the eye. Criteria used to evaluate success include the percentage of self-sealing incisions/wounds immediately after cannula removal, post-operative intraocular pressure maintenance, post-operative pain, incidence of endophthalmitis, time to perform the procedure, and difficulties experienced when performing the procedure.

Variations between surgical procedures, however, have made it more difficult to evaluate and determine optimal surgical techniques and methods, such as insertion angle of the trocar. For example, previous surgical devices used in ophthalmic procedures provide widely varying patient outcomes and recovery times due to variables such as surgical technique, training, or expertise, as well as variance in surgical instruments, including shape, sharpness, and size of trocars and cannulas used in the procedure. Accordingly, an improved surgical device is needed to provide improved and more consistent patient outcomes and recovery times.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a surgical device includes a trocar, a cannula mounted on the trocar, a propulsion system connected to the trocar, and a positioner disposed at a distal end of the surgical device. The cannula includes a hub and has a central opening through which the trocar extends. The propulsion system is operable to drive the trocar axially in a forward direction away from a proximal end of the surgical device. The positioner includes an engagement member having a contoured engagement surface that, when engaged with an eye of a patient, causes the trocar to be oriented relative to the eye at a predetermined oblique entry angle.

In another aspect, a method of using a surgical device to insert a trocar-cannula assembly into eye tissue includes a propulsion system connected to the trocar-cannula assembly, and a positioning member disposed at a distal end of the surgical device. The method includes engaging the eye tissue with the positioning member, where engaging the eye tissue with the positioning member causes the trocar-cannula assembly to be oriented at a predetermined oblique entry angle relative to the eye tissue, activating the propulsion system, and driving the trocar-cannula assembly with the propulsion system into the eye tissue at the predetermined oblique entry angle.

In yet another aspect, a surgical device for incising eye tissue includes a trocar-cannula assembly, a propulsion system connected to the trocar-cannula assembly and operable to drive the trocar-cannula assembly axially in a forward direction away from a proximal end of the surgical device, and a positioning member disposed at a distal end of the surgical device. The trocar-cannula assembly includes a trocar and a cannula releasably mounted on the trocar. The cannula includes a hub and has a central opening through which the trocar extends. The positioning member includes an engagement member having a contoured engagement surface for engagement with eye tissue. The propulsion system is operable to displace the trocar-cannula assembly by a stroke length and stop forward movement of the trocar-cannula assembly to prevent the hub of the cannula from moving axially past the engagement surface.

In yet another aspect, a surgical device includes a trocar, a cannula mounted on the trocar, and a propulsion system connected to the trocar and operable to drive the trocar axially in a forward direction away from an end of the surgical device. A collar is also connected to the propulsion system, and the cannula includes a hub and a central opening through which the trocar extends. The collar can be used to remove the cannula from the trocar after the propulsion system is activated.

In yet another aspect, a surgical device includes a trocar, a cannula mounted on the trocar, and a propulsion system connected to the trocar and operable to drive the trocar axially in a forward direction away from a proximal end of the surgical device. A trocar retraction mechanism is connected to the trocar. The cannula includes a hub and has a central opening through which the trocar extends. The trocar retraction mechanism can be used to automatically retract the trocar after the propulsion system is activated.

In yet another aspect, a surgical device includes a plurality of trocar-cannula assemblies and a plurality of propulsion systems. Each of the trocar-cannula assemblies includes a trocar and a cannula releasably mounted on the trocar. The cannula includes a hub and has a central opening through which the trocar extends. Each of the propulsion systems is connected to a corresponding trocar-cannula assembly, and is operable to drive the corresponding trocar-cannula assembly axially in a forward direction away from a proximal end of the surgical device.

In yet another aspect, a surgical device includes a trocar, a cannula releasably mounted on the trocar, and a propulsion system operatively connected to the trocar. The cannula includes a hub and has a central opening through which the trocar extends. The propulsion system is operable to drive the trocar axially in a forward direction away from a proximal end of the surgical device.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

BRIEF DESCRIPTION OF THE DRAWINGS

Corresponding reference characters indicate corresponding parts throughout the several views of the drawings.

DETAILED DESCRIPTION

Figure 1:
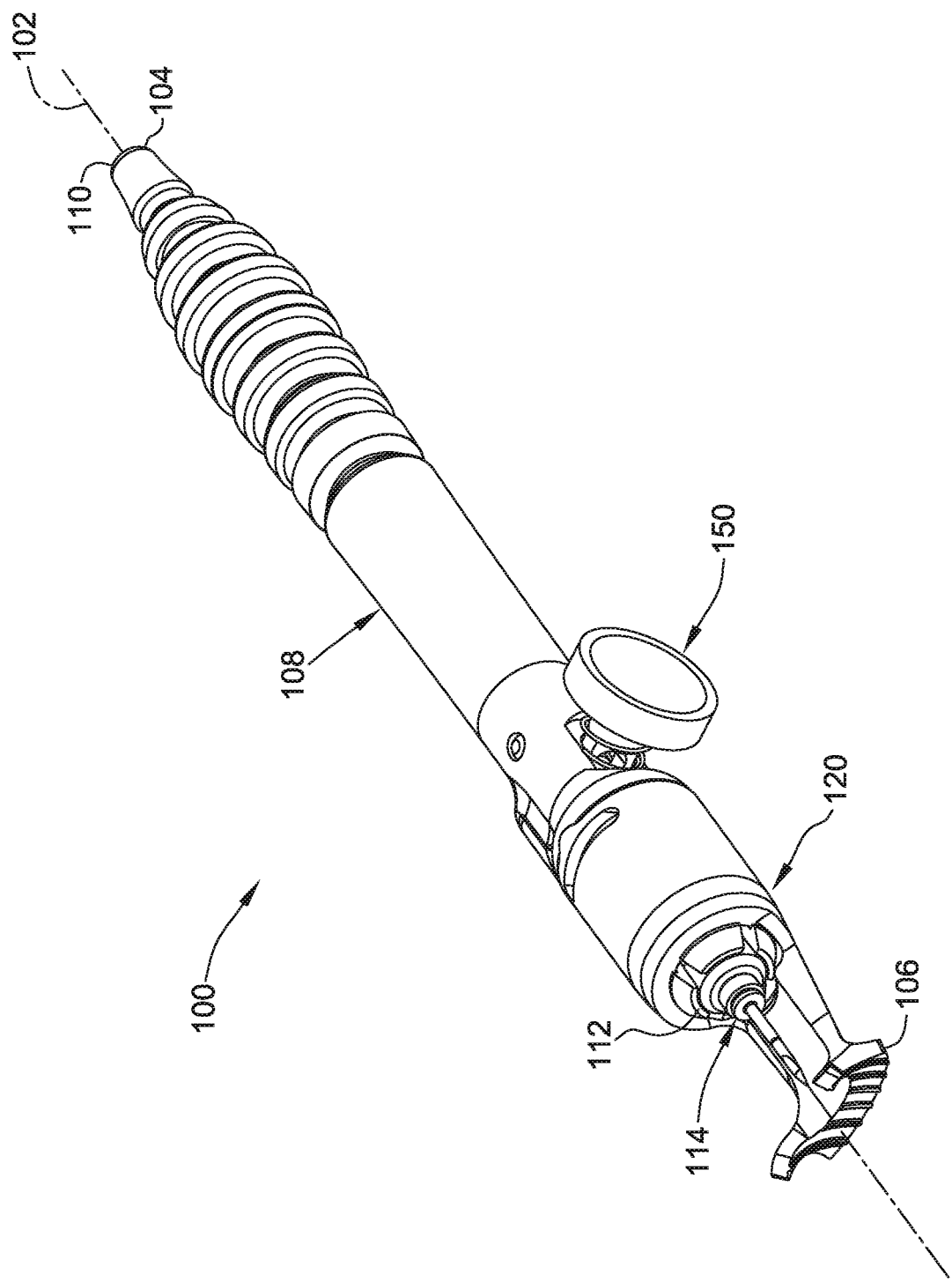
FIG. 1 is a perspective of an embodiment of a surgical device including a propulsion or actuation system for inserting a trocar-cannula assembly into a patient.

Embodiments of the systems and methods described herein are designed to improve patient outcomes and recovery times following surgical procedures, such as ophthalmic produces, by reducing strain and trauma imparted to tissue during the surgical procedure, and by providing consistent, optimal wound geometries at incision sites. The present disclosure provides examples of surgical devices and methods designed to produce consistent wound geometries and incision entry angles into the eye regardless of varying factors, such as surgeon technique, training, or expertise, and manufacturing variances in surgical instruments, such as the shape, sharpness, and size of trocars and cannulas used in surgical procedures. Additionally, embodiments of the surgical devices and methods described herein facilitate accurate placement of incisions in the Pars Plana for ophthalmic procedures without reliance on additional instrumentation, reduce deflection of the eye during cannula insertion, and reduce the amount of intraocular pressure rise experienced by the eye during cannula insertion.

As noted above, several studies have been performed to evaluate the success of methods used to gain access to the posterior chamber of the eye. One surgical technique that has been shown to improve outcomes in ophthalmic procedures is creation of the sclerotomy at an angle relative to the wall of the sclera. The angled incision allows the positive (relative to atmosphere) pressure inside the eye (i.e., the intraocular pressure) to help close the wound after the instrument cannula is removed. Viewed strictly from an initial ability for the wound to seal, the ideal insertion angle is nearly tangential to the scleral wall. In practice this type of wound is impractical because a small error in the insertion angle can result in the instrument cannula being too short to fully enter the posterior chamber with the accompanying risk of detachment complications when instruments are inserted. In addition, the strain put onto the tissue around the incision is increased as the position of the cannula is twisted to allow instrument access into the various portions of the posterior chamber, which compromises the tissues ability to recover its shape and seal. However, efforts to determine the optimal insertion angle have been complicated by difficulties in consistently controlling the insertion angle of the trocar and cannula. Variations in surgeon technique, instrument quality, instrument design, intraocular pressure, scleral toughness and other variables can all contribute to variation in the incision angle.

Wound geometry has also been shown to influence surgery outcomes. For example, the shape, size, and sharpness of the cutting tip of the trocar determine the shape, length, and quality (e.g., cleanly cut vs. torn) of the resulting wound. Additionally, the shape and length of the wound relative to the outside diameter of the instrument cannula determines the amount of strain applied to the tissue by the instrument cannula. A cleanly cut straight incision that is barely large enough to stretch around the instrument cannula with minimized strain to the surrounding tissue yields optimal results. This type of wound seals well after the instrument cannula is removed, and tends to resist inadvertent cannula removal because of the tension of the tissue around the instrument cannula. Manufacturing variations in trocar sharpness can have a significant effect on how cleanly cut the wound is.

The configuration of the cannula to trocar shaft interface can also influence the ease of cannula insertion, wound geometry, and wound sealing. For example, larger differences between the trocar diameter and the instrument cannula diameter increase the requirements for the tissue to stretch around the cannula. If the tissue is strained beyond its elastic limit, then tearing can occur and both cannula retention and wound sealing are compromised. The shape of the distal end (the end that enters the eye first) of the instrument cannula can ease the initial entry of the cannula into the incision, but has little effect on the ultimate amount of strain caused to the tissue upon cannula insertion.

Variability in manufacturing tolerances, surgeon technique, and instrument designs can lead to a large variance in patient outcomes and surgeon comfort level. For example, a trocar that is less sharp than ideal requires significantly more force to create an incision, and can yield an incision that is less capable of sealing. The increase in force also presents a challenge to the surgeon because the eye tends to push away from the trocar and requires counter force to maintain the desired position during trocar insertion. As the force required for trocar insertion increases, controlling the position of the eye becomes more difficult.

Embodiments of the systems and methods described herein are designed to facilitate reducing strain and trauma imparted to tissue during surgical procedures, and to facilitate consistent, optimal wound geometries at incision sites. In particular, the present disclosure provides example surgical devices and methods that include a triggered drive or propulsion system configured to drive a trocar-cannula assembly with a force and velocity greater than that practically achievable by manual manipulation. The force and velocity imparted to the trocar-cannula assembly is sufficiently high such that the inertia of the tissue incised by the trocar is not overcome to a significant degree by the force generated during the creation of the incision and subsequent insertion of the cannula. Additionally, the system is operable to precisely control the stroke length of the trocar-cannula assembly to enable optimal insertion of the trocar-cannula assembly without exerting excessive pressure on the tissue in which the trocar-cannula assembly is inserted, and without inserting the assembly to less than or greater than optimal depth. For example, in some embodiments, the propulsion system is configured to stop the trocar-cannula assembly at a point just prior to a hub of the cannula contacting the tissue into which the trocar is inserted. Additionally, embodiments of the surgical devices and methods described herein utilize a positioning member to facilitate consistent positioning and orientation of the trocar prior to insertion of the trocar at the surgical site. The positioning member thereby facilitates producing consistent wound geometries and incision entry angles into the eye regardless of varying factors, such as surgeon technique, training, or expertise.

Figure 2:
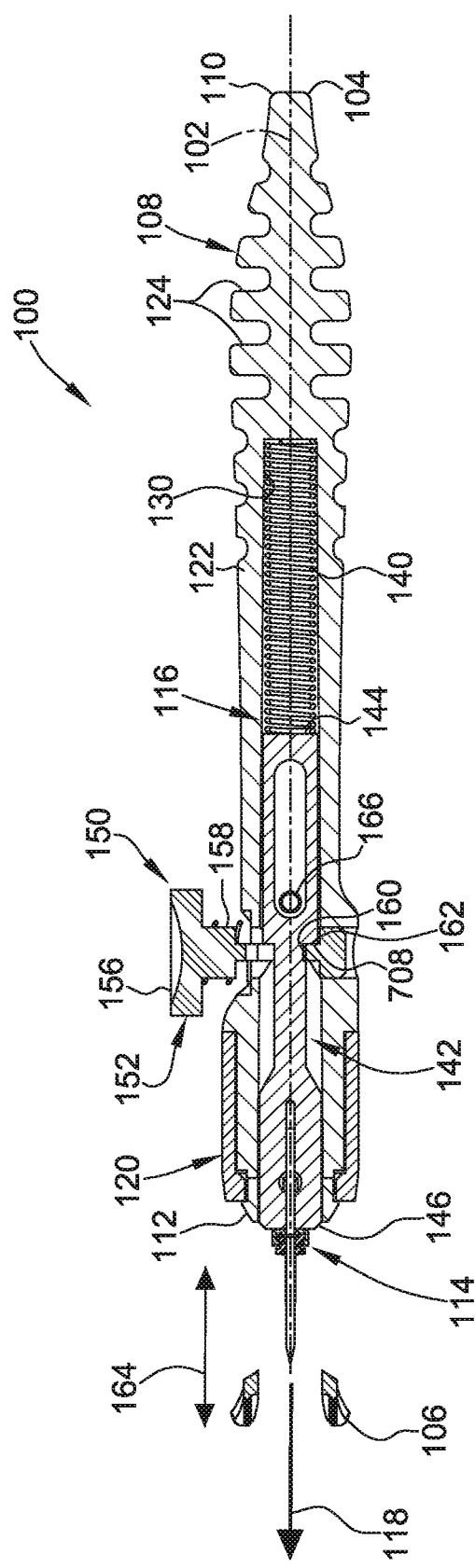
FIG. 2 is a cross-sectional view of the surgical device of FIG. 1.
Figure 3:
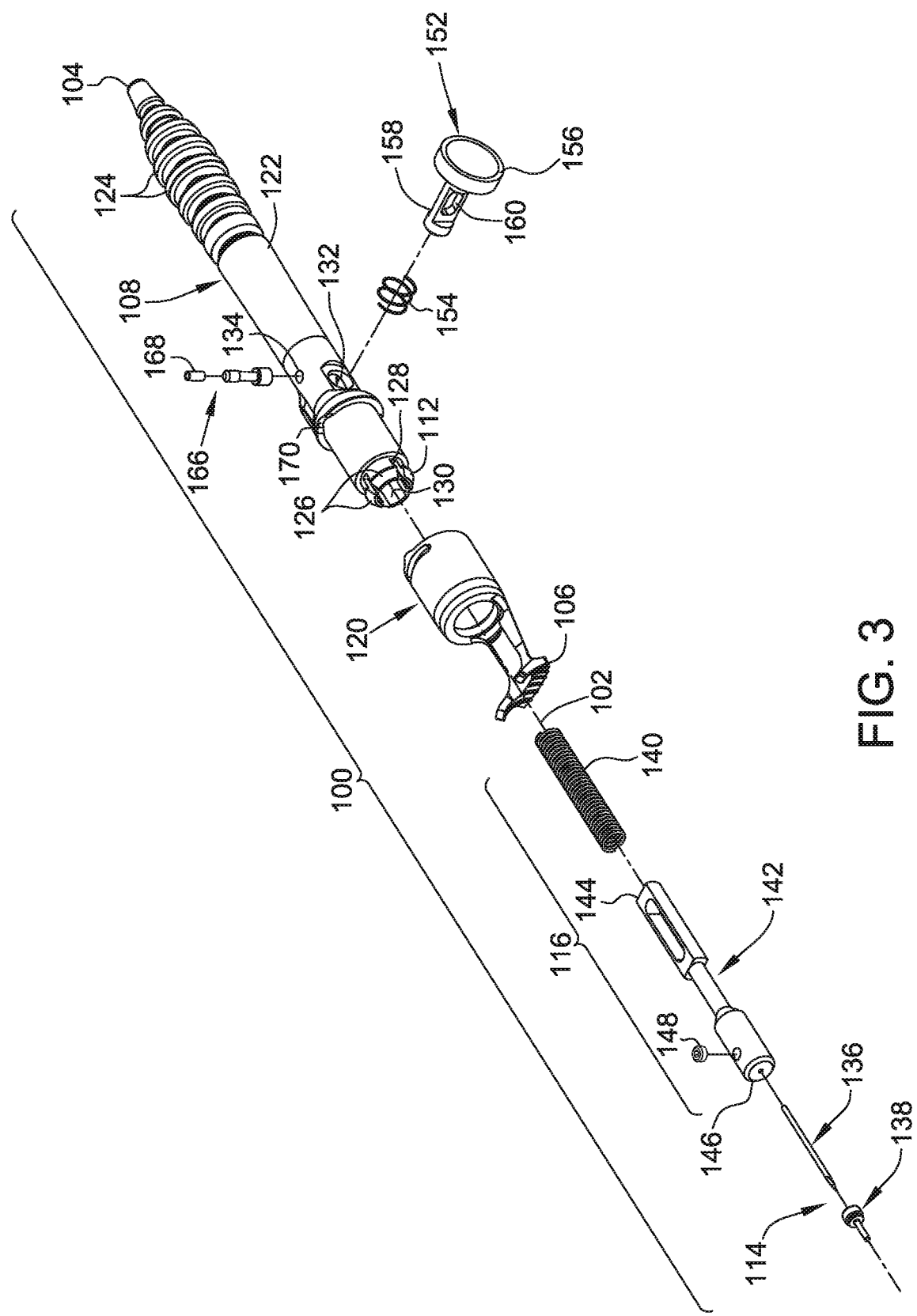
FIG. 3 is an exploded view of the surgical device of FIG. 1.

FIG. 1 is a perspective view of a surgical device 100 including a triggered drive system (which may also be referred to as a propulsion system or an autoinserter) for driving a trocar-cannula assembly into a tissue or organ. FIG. 2 is a cross-section of the surgical device 100, and FIG. 3 is an exploded view of the surgical device 100. As shown in FIGS. 1-3, the surgical device 100 extends a length along a central longitudinal axis 102 from a first, proximal end 104 to a second, distal end 106. The surgical device 100 generally includes a handle 108 having a proximal end 110 and an opposing distal end 112, a trocar-cannula assembly 114 disposed at the distal end 112 of the handle 108, and a propulsion system 116 configured to axially drive or propel the trocar-cannula assembly 114 in a forward direction (i.e., away from the proximal end 110 of the handle 108) indicated by arrow 118 in FIG. 2. The surgical device also includes a positioner or positioning member 120 disposed at the distal end 112 of the handle 108. The positioning member 120 is configured to facilitate alignment of the surgical device 100 relative to a patient's eye, and stabilize the surgical device 100 during surgical procedures.

The surgical device 100 may be used in various surgical procedures. In the example embodiment, the surgical device 100 is particularly suitable for use in ophthalmic procedures including, for example and without limitation, vitrectomies, membranectomies, and photocoagulation. The surgical device 100 may be used, for example, to incise the sclera of a patient's eye, and to insert the trocar-cannula assembly 114 through the sclera to provide access to the posterior segment of the eye. In the example embodiment, the surgical device 100 is particularly suited for use on humans, although in other embodiments, the surgical device 100 may be modified for non-human use, such as for veterinary procedures.

The handle 108 includes a generally cylindrical body 122 extending from the distal end 112 of the handle 108 to the proximal end 110 of the handle 108. The body 122 of the handle 108 is ergonomically shaped to facilitate gripping and manipulation of the surgical device 100. In the illustrated embodiment, the handle 108 includes tactile ridges 124 to further facilitate gripping and manipulation of the surgical device 100. In the illustrated embodiment, the tactile ridges 124 are disposed between a midpoint of the handle 108 and the proximal end 110 of the handle 108, although other embodiments may include tactile ridges located at other locations along the handle 108. In yet other embodiments, the handle 108 may not include any tactile ridges.

The handle 108 also includes a plurality of retention tabs 126 securing the positioning member 120 to the distal end 112 of the handle 108. The retention tabs 126 are disposed at the distal end 112 of the handle 108, and are circumferentially spaced about the longitudinal axis 102 of the surgical device 100. Adjacent retention tabs 126 are separated from one another by a slit 128 extending axially into the handle 108 from the distal end 112. The retention tabs 126 are configured to deflect radially inward as the positioning member 120 is slid over the distal end 112 of the handle 108, and return to their initial, undeflected position (shown in FIGS. 2 and 3) to inhibit axial movement of the positioning member 120.

As shown in FIG. 2, the body 122 of the handle 108 defines a cavity 130 in which components of the propulsion system 116 are housed. The cavity 130 is suitably sized and shaped to permit components of the propulsion system 116 to be housed therein. In the illustrated embodiment, the cavity 130 has a circular cross-section, and is configured to permit axially movement of components of the propulsion system 116 therethrough.

In the illustrated embodiment, the body 122 also defines a pair of triggering device openings 132 and a pair of stop pin openings 134. Each of the triggering device openings 132 and the stop pin openings 134 extends radially through the body 122 of the handle 108. Further, each of the triggering device openings 132 is located on a diametrically opposite side of the body 122 from the other of the triggering device openings 132, and each of the stop pin openings 134 is located on a diametrically opposite side of the body 122 from the other of the triggering device openings 132. The triggering device openings 132 are suitably sized and shaped to receive at least a portion of a triggering device, described in more detail herein. The stop pin openings 134 are suitably sized and shaped to receive at least a portion of a stop pin, described in more detail herein.

The handle 108 can be constructed of suitably rigid or semi-rigid materials, including, for example and without limitation, plastics, polymers, metals, composites, and combinations thereof. In certain embodiments, portions of the handle 108 may be constructed of a flexible material, including, for example and without limitation, silicone or similar elastomeric or flexible polymers.

Figure 4:
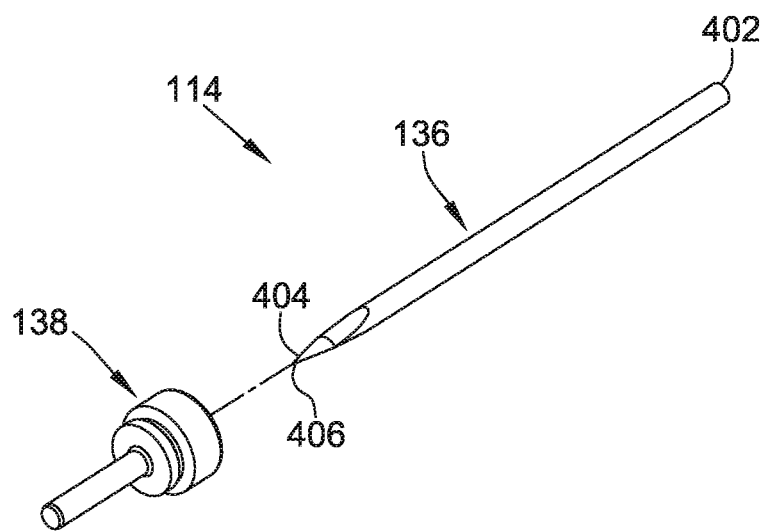
FIG. 4 is an exploded view of the trocar-cannula assembly of the surgical device of FIG. 1, the trocar-cannula assembly including a trocar and a cannula.

The trocar-cannula assembly 114 includes a trocar 136 and a cannula 138 releasably mounted on the trocar 136. FIG. 4 is an enlarged exploded view of the trocar-cannula assembly 114. As shown in FIG. 4, the trocar 136 has a proximal end 402 and a distal end 404. The distal end 404 of the trocar 136 includes a cutting tip 406 for piercing or incising organs or tissue, such as the sclera of an eye. The cutting tip 406 may be beveled, tapered, and/or sharpened to facilitate insertion of the trocar 136. Suitable configurations for the trocar 136 include hypodermic needles, lancet-shaped needles, stiletto blades, saber-tipped blades, beveled rods, and any other configuration suitable for making a stab incision in a tissue or organ. The trocar 136 may be constructed of suitably rigid materials, including, for example and without limitation, stainless steel. In some embodiments, the trocar 136 is sized for use in ophthalmic surgical procedures. For example, the trocar 136 may have an outer diameter of between about 20-gauge (0.91 mm) and about 27-gauge (0.41 mm). In some embodiments, the trocar 136 has an outer diameter less than or equal to 23-gauge (0.64 mm), less than or equal to 25-gauge (0.51 mm), or even less than or equal to 27-gauge. In other embodiments, the trocar 136 may have an outer diameter greater than 20-gauge.

Figure 5:
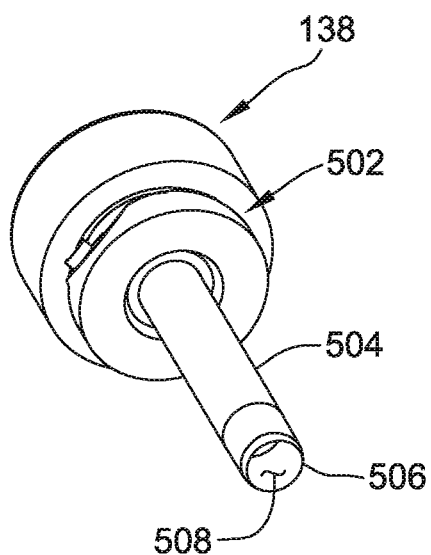
FIG. 5 is a perspective of the cannula of the trocar-cannula assembly of FIG. 4.

FIG. 5 is an enlarged perspective view of the cannula 138. As shown in FIG. 5, the cannula 138 includes an annular flange or hub 502 and a hollow shaft 504 extending from the hub 502 to a distal end 506 of the cannula 138. The shaft 504 has a smooth outer surface, and defines a central opening 508 sized and shaped to receive the trocar 136 therein. The inner diameter of the cannula shaft 504 may be sized just larger than an outer diameter of trocar 136 to minimize the step (i.e., the difference in diameters) between the trocar 136 and the cannula 138. Minimizing or limiting the change in diameter from the trocar 136 to the cannula 138 facilitates insertion of the trocar-cannula assembly 114 into tissue, and minimizes or limits the strain on the tissue during insertion. In some embodiments, the inner diameter of the cannula shaft 504 is between about 20-gauge and about 27-gauge. In some embodiments, the inner diameter of the cannula shaft 504 is less than or equal to 23-gauge, less than or equal to 25-gauge, or even less than or equal to 27-gauge. In other embodiments, the inner diameter of the cannula shaft 504 is greater than 20-gauge. In some embodiments, a portion of the cannula shaft 504 (such as the distal end) is swaged or tapered radially inward to a diameter substantially equal to the diameter of the trocar 136. In such embodiments, the cannula 138 may be press fit onto the trocar 136 to provide the minimal amount of friction between the cannula 138 and trocar 136 needed to maintain the position of the cannula 138 on the trocar 136 when the propulsion system 116 is activated.

The cannula 138 may be constructed of rigid materials, including, for example and without limitation, stainless steel, titanium, and combinations thereof. Additionally or alternatively, the cannula 138 may be constructed of flexible materials, including, for example and without limitation, plastics, such as polyamide. The cannula 138 may be constructed of the same materials as the trocar 136, or the cannula 138 may be constructed of different materials than the trocar 136.

Figure 6:
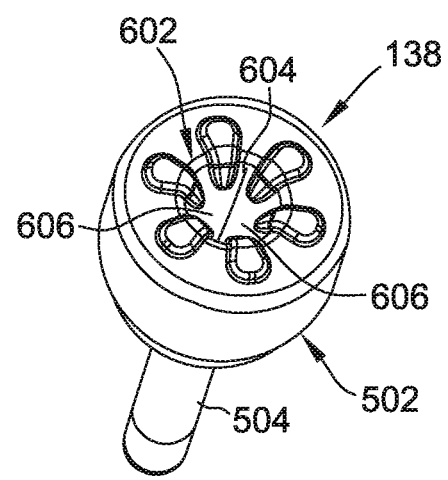
FIG. 6 is another perspective of the cannula of FIG. 5 showing a valve of the cannula.

In some embodiments, such as the embodiment illustrated in FIG. 6, the cannula 138 includes a valve 602 operable to inhibit or restrict fluid flow through the cannula 138 (specifically, through the central opening 508). In the illustrated embodiment, the valve 602 is made of or includes a flexible, resilient material, including, for example and without limitation, silicone. Other suitable materials from which the valve 602 may be made of include, for example and without limitation, polyurethane, PVC, and other medical grade elastomers. The valve 602 has a slit 604 defined therein to allow insertion of the trocar 136 (and other surgical instruments) therethrough. The slit 604 defines two valve members 606 that deflect from an initial position (shown in FIG. 6) when the trocar 136 is inserted through the valve 602. When the trocar 136 is removed from the valve 602, the valve members 606 return to the initial position, and seal the cannula opening 508 to inhibit fluid flow therethrough. In the illustrated embodiment, when the trocar-cannula assembly 114 is assembled, the valve members 606 are biased against and engage the trocar 136, and provide a resistive frictional force sufficient to maintain the position of the cannula 138 relative to the trocar 136. The valve 602 and trocar 136 are constructed of materials with suitable coefficients of friction such that the resistive frictional forces between the valve 602 and the trocar 136 are sufficient to maintain the position of the cannula 138 on the trocar 136 when the propulsion system 116 is activated. In some embodiments, for example, the valve is constructed of silicone, and the trocar is constructed of stainless steel.

The propulsion system 116 is operatively connected to the trocar-cannula assembly 114, and is operable to propel or drive the trocar-cannula assembly 114 in the forward direction 118 when activated by a user of the surgical device 100. The propulsion system 116 can include any suitable electrical, mechanical, and/or electromechanical devices for generating and/or transmitting kinetic energy to the trocar-cannula assembly 114 to drive the trocar-cannula assembly 114 in the forward direction 118. In some embodiments, the propulsion system 116 includes at least one spring-driven piston. In some embodiments, the propulsion system 116 may include a pneumatically-driven piston and/or a hydraulically-driven piston. In some embodiments, the propulsion system 116 may include one or more diaphragms driven by a spring, a pneumatic system, or a hydraulic system. In some embodiments, the propulsion system 116 may include a solenoid assembly including, but not limited to, a solenoid coil and a piston, and a rotary solenoid and a transmission member to convert rotational motion of the rotary solenoid to linear motion. In some embodiments, the propulsion system 116 may include an electric motor and a suitable transmission member to transmit motion from the motor to the trocar-cannula assembly 114. Suitable transmission members include, but are not limited to, worm gear drives and rack and pinion assemblies. Other devices suitable for use in or as a propulsion system include, but are not limited to, speaker coils, electromagnets, permanent magnets, shape memory alloys, and piezoelectric materials.

In some embodiments, the propulsion system 116 generally includes a drive member configured to generate kinetic energy, and a transmission member configured to transmit the kinetic energy from the drive member to the trocar-cannula assembly 114. In the illustrated embodiment, the propulsion system 116 includes a drive member in the form of a helical spring 140, and a transmission member in the form of a piston 142. In some embodiments, such as the embodiment illustrated in FIGS. 2 and 3, the propulsion system 116 is configured (e.g., sized and shaped) to fit within the cavity 130 of the handle 108. In other embodiments, components of the propulsion system 116 may be integrated within the body 122 of handle 108, and/or coupled to the body 122 of handle 108.

As shown in FIG. 2, the spring 140 is disposed within the cavity 130 defined by the body 122, and is compressible between the piston 142 and the proximal end 110 of the handle 108. The piston 142 is axially moveable under the force of the spring 140 between a first, retracted position (shown in FIG. 2), and a second, extended position (shown in FIGS. 9 and 10). The piston 142 is connected to the spring 140 at a first, proximal end 144 of the piston 142, and is connected to the trocar-cannula assembly 114 at a second, distal end 146 of the piston 142.

Figure 7:
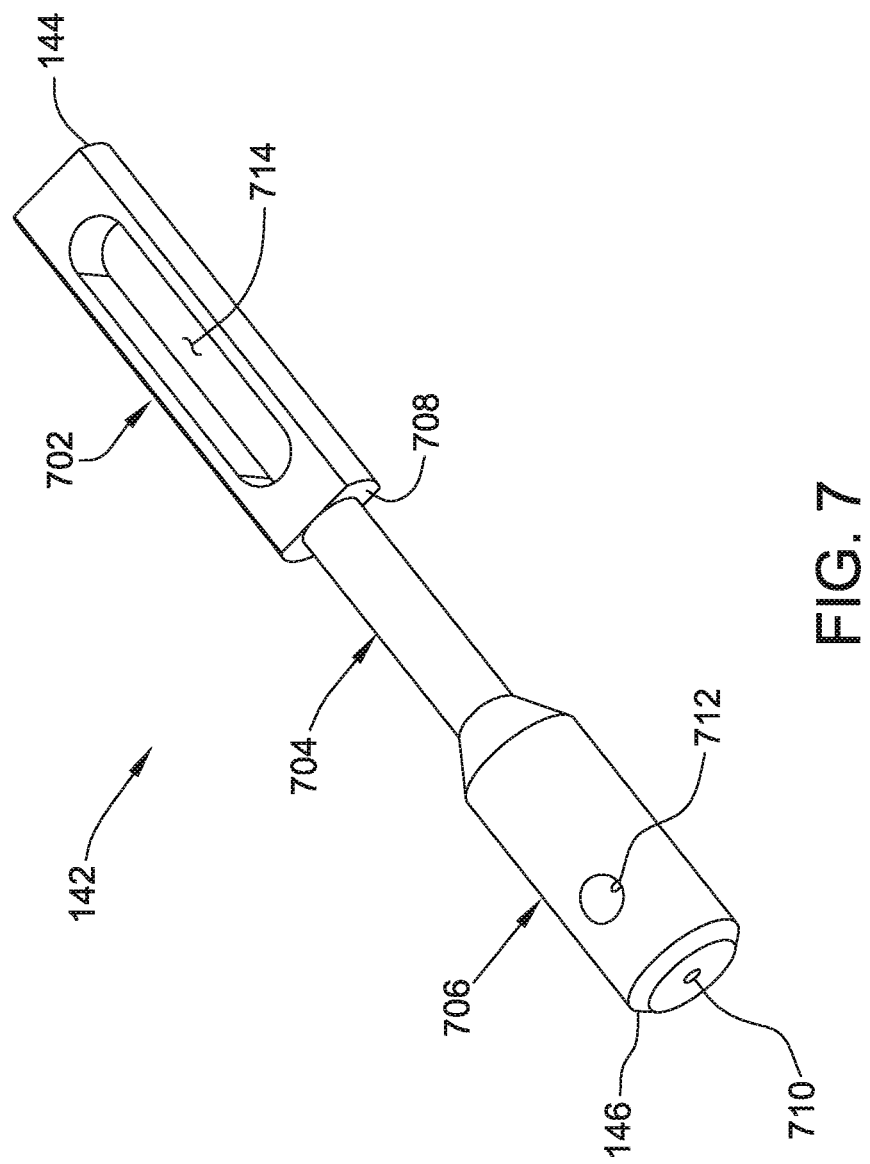
FIG. 7 is a perspective of a piston suitable for use in the propulsion system of the surgical device of FIG. 1.

FIG. 7 is a perspective view of the piston 142 from the propulsion system 116. As shown in FIG. 7, the piston 142 includes a first portion 702, a second portion 704, and a third portion 706. The first portion 702 has rectangular or pseudo-rectangular cross-section, and has a width or diameter greater than the second portion 704. The first portion 702 adjoins the second portion 704 at a lip 708. The second portion 704 has a substantially circular cross-section, and has a width or diameter less than each of the first portion 702 and the third portion 706. The second portion 704 is disposed between and interconnects the first portion 702 and the third portion 706.

The third portion 706 of the piston 142 is configured for connection to the trocar-cannula assembly 114 to secure the trocar-cannula assembly 114 to the piston 142, and is also referred to herein as a trocar holder. In the illustrated embodiment, the third portion 706 includes a trocar opening 710 extending axially into the piston 142 from the distal end 146. The trocar opening 710 is sized and shaped to receive the trocar 136 therein. The third portion 706 also includes a fastener opening 712 extending radially into and through the piston 142. The fastener opening 712 is sized and shaped to receive a fastener, such as a set screw, therein to secure the trocar 136 to the third portion 706 of the piston 142. When the surgical device 100 is assembled, the proximal end 402 of the trocar 136 extends into the trocar holder 706, and is fixed to the trocar holder 706 by suitable connection means. In the illustrated embodiment, the trocar 136 is secured to the trocar holder 706 with a set screw 148 (shown in FIG. 2). In other embodiments, the trocar 136 may be secured to the trocar holder 706 using any suitable connection means that enables the surgical device 100 to function as described herein. In some embodiments, for example, the trocar holder 706 may be over-molded onto the trocar 136. In yet other embodiments, the trocar 136 and the trocar holder 706 may be formed as a single, integral piece, for example, by casting or molding.

In the illustrated embodiment, the first portion 702 of the piston 142 has an elongate slot 714 defined therein. The slot 714 is elongate in the direction of motion of the propulsion system 116, which, in the illustrated embodiment, is parallel to the longitudinal axis 102 of the surgical device 100. The elongate slot 714 is sized and shaped to receive a stop pin therein to control a stroke length of the propulsion system 116, as described in more detail herein.

As noted above, the propulsion system 116 is configured to drive or propel the trocar-cannula assembly 114 with a force and velocity greater than that typically applied by manual manipulation. In particular, the propulsion system 116 is configured to drive the trocar 136 and cannula 138 with a sufficient force and velocity such that the inertia of the tissue incised by the trocar 136 is not overcome to a significant degree by the force generated during the creation of the incision and subsequent insertion of the cannula 138. As a result, production tolerances or imperfections in the cutting tip 406 of the trocar 136 have less of an effect on the wound geometry because the tissue inertia tends to greatly increase the stress transmitted to the tissue as compared to a manual incision with the same trocar. The propulsion system 116 thereby provides a cleaner cut as compared to manually inserted trocars, and imparts less stress to surrounding tissue (outside the area of the incision) as compared to manually inserted trocars. Additionally, because the tissue moves less during the insertion, the intraocular pressure is affected to a much lower degree than with the manually inserted trocars.

The surgical device 100 also includes a trigger or activation device 150 operatively connected to the propulsion system 116, and operable to activate the propulsion system 116 in response to user input. Although the activation device 150 is shown as being directly connected to the surgical device 100 in the illustrated embodiment, the activation device 150 may be located remotely from the surgical device 100 in other embodiments. In such embodiments, the activation device 150 may communicate with an electromechanical device operatively connected to the propulsion system 116 to activate the propulsion system 116.

In the illustrated embodiment, the activation device 150 is a manually actuated trigger mechanism. Specifically, the activation device 150 includes a depressible knob or trigger 152 moveable between a first, undepressed position and a second, depressed position, and a helical trigger spring 154 configured to bias the trigger 152 towards the first position. The trigger 152 includes a head 156 connected to a shaft 158 that extends radially through the handle 108 (specifically, through the triggering device openings 132). The head 156 has an enlarged, pronounced diameter relative to the shaft 158 to provide an adequate area for a user to engage and depress the trigger with a thumb or finger. The trigger spring 154 is disposed between the head 156 of the trigger 152 and a radial outer surface of the body 122 to bias the trigger 152 in a radially outward direction.

The trigger 152 has a piston opening 160 defined therein sized and shaped to receive a portion of the piston 142 therein. In the illustrated embodiment, the piston opening 160 has a cross-section sized and shaped complementary to the first portion 702 of the piston 142 to permit the first portion 702 of the piston 142 to pass therethrough. As shown in FIG. 2, when the trigger 152 is in the first position, the piston opening 160 is offset or out of alignment with the first portion 702 of the piston 142. A portion of the shaft 158 engages the lip 708, and acts as a latch 162 to inhibit forward axial movement of the piston 142. When the trigger is depressed from the first position to the second position, the piston opening 160 is aligned with the first portion 702 of the piston 142, and the latch 162 disengages the lip 708, allowing the piston 142 to move axially forward under the force of the spring 140.

Figure 9:
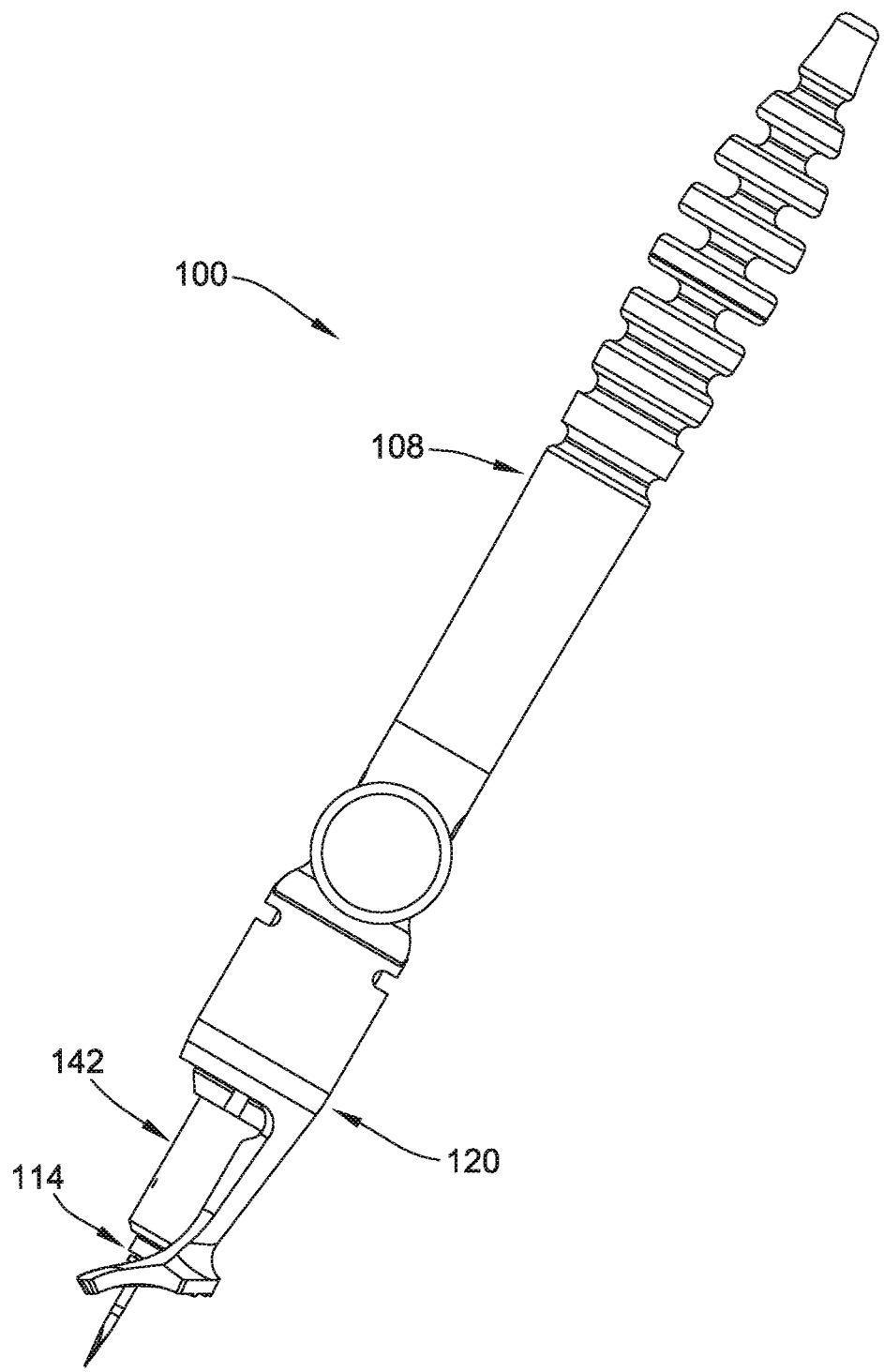
FIG. 9 is a side view of the surgical device of FIG. 1 showing the trocar-cannula assembly in an extended position.
Figure 10:
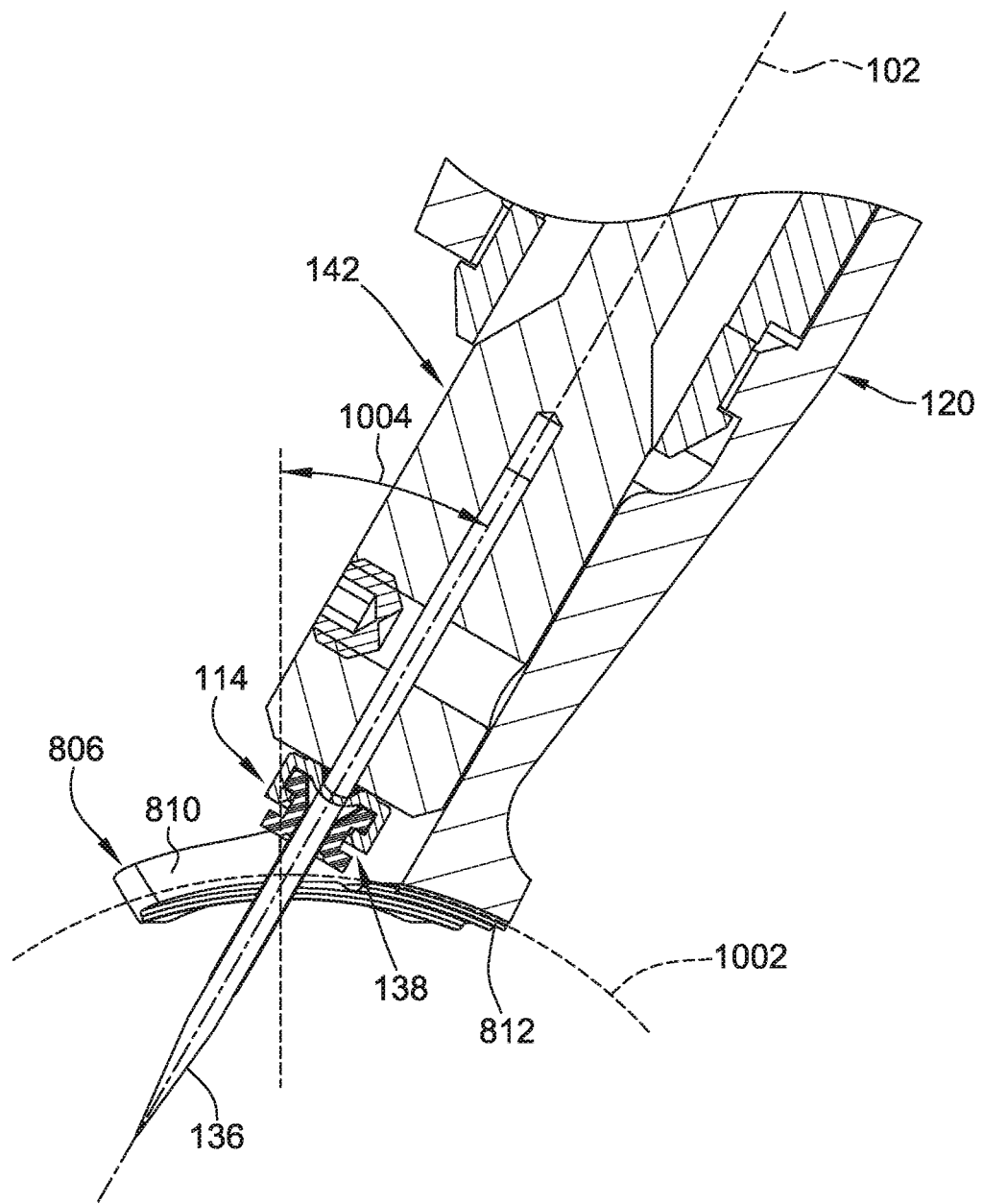
FIG. 10 is an enlarged cross-sectional view of the surgical device of FIG. 9.

The propulsion system 116 is configured to move the trocar-cannula assembly 114 axially in the forward direction 118 a stroke length 164, measured as the axial displacement of the trocar-cannula assembly 114 between the initial, unfired position (shown in FIG. 1), and the extended, fired position (shown in FIGS. 9 and 10). The propulsion system 116 is configured to provide an optimal stroke length 164 of the trocar-cannula assembly 114 to enable optimal insertion of the trocar-cannula assembly 114 without exerting excessive pressure on the tissue in which the trocar-cannula assembly 114 is inserted. In particular, the propulsion system 116 is configured to stop the trocar-cannula assembly 114 just prior to the hub 502 of the cannula 138 contacting the tissue into which the trocar 136 is inserted. In the illustrated embodiment, the propulsion system 116 includes a stop pin 166 configured to limit and precisely control the stroke length 164 of the trocar-cannula assembly 114.

The stop pin 166 is positioned within the stop pin openings 134 defined by the body 122 of the handle 108, and extends radially through the body 122. When the surgical device 100 is assembled, the stop pin 166 is positioned within the slot 714 defined by the first portion 702 of the piston 142. The stop pin 166 is configured to engage the piston 142 to limit axial movement of the piston 142. Specifically, the stop pin 166 is configured to engage the first portion 702 of the piston 142 along inner surfaces of the piston 142 that define the slot 714. The slot 714 has a length substantially equal to the stroke length 164 of the trocar-cannula assembly 114. As shown in FIG. 3, the stop pin 166 includes a bearing collar or sleeve 168 to minimize or limit friction between the stop pin 166 and the piston 142.

As noted above, the propulsion system 116 is configured to drive or propel the trocar-cannula assembly 114 with a force and velocity greater than that typically applied by manual manipulation. The propulsion system 116 may be configured to complete a stroke length of the trocar-cannula assembly 114 within a certain amount of time, such as within 1 second, within 0.5 seconds, or even within 0.1 seconds. Further, in some embodiments, the propulsion system 116 may be configured to move the trocar-cannula assembly 114 at a certain velocity, such as between 0.05 m/s and 1 m/s, or between 0.1 m/s and 1 m/s. In other embodiments, the propulsion system 116 may be configured to move the trocar-cannula assembly 114 at a velocity less than 0.05 m/s, or at a velocity greater than 1 m/s.

Figure 8:
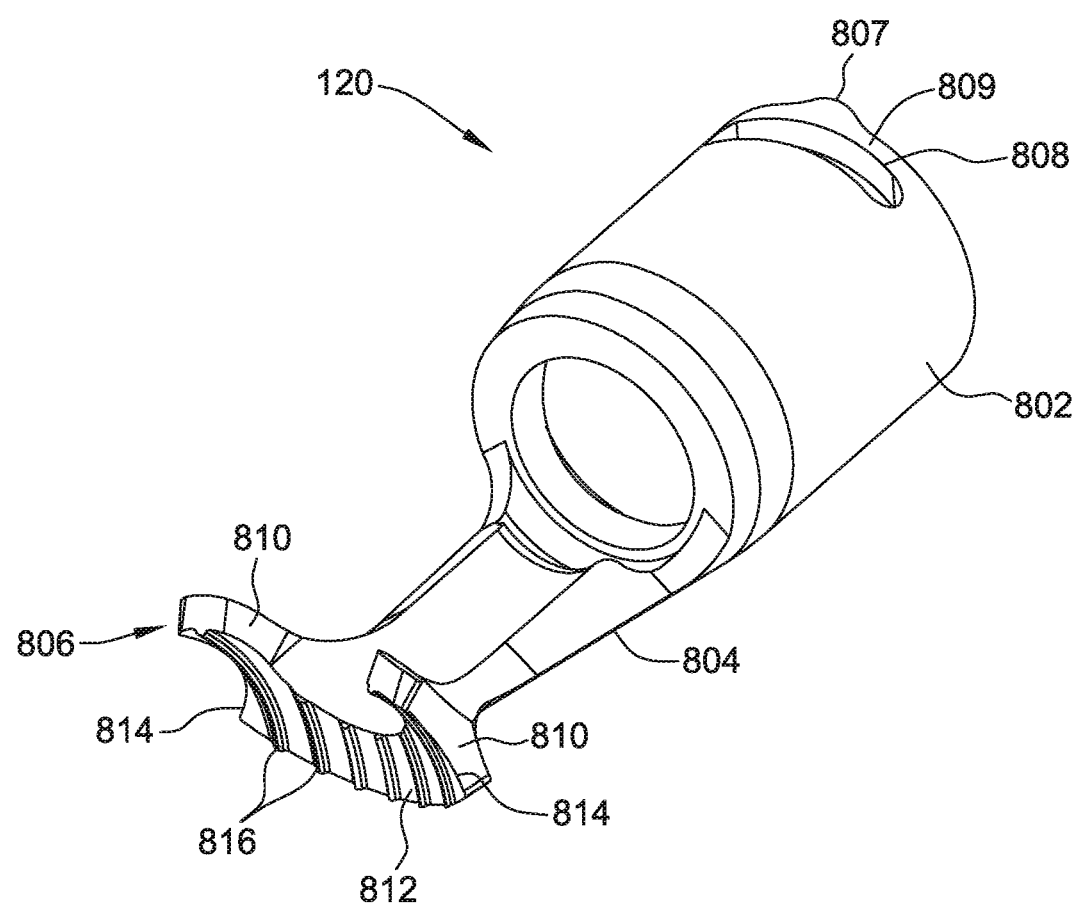
FIG. 8 is a perspective of a positioning member of the surgical device of FIG. 1.

Referring again to FIGS. 1-3, the positioning member 120 is configured to engage a generally spherical surface, such as the sclera of an eye, to align the surgical device 100 (specifically, the trocar-cannula assembly 114) with a desired incision site on the eye, and to stabilize the surgical device 100 during activation of the propulsion system 116. FIG. 8 is a perspective view of the positioning member 120 shown in FIGS. 1-3. As shown in FIG. 8, the positioning member 120 generally includes a connector portion 802 configured for connection to the distal end 112 of the handle 108, a leg 804 extending distally from the connector portion 802, and an engagement member 806 disposed at a distal end of the leg 804.

The connector portion 802 is configured for connection to the handle 108 to fix the positioning member 120 relative to the handle 108. In the illustrated embodiment, the connector portion 802 is a sleeve having an inner diameter sized and shaped to receive the distal end 112 of the handle 108 therein. When the surgical device 100 is assembled, a distal end of the connector portion 802 engages the retention tabs 126 of the handle 108, and a proximal end of the connector portion engages a lip on the handle 108 to prevent axial movement of the positioning member 120 relative to the handle 108. In other embodiments, the connector portion 802 may include any suitable connecting structure that enables the connector portion 802 to connect to the handle, including, for example and without limitation, threads.

The connector portion 802 also has a pair of alignment protrusions 807 disposed diametrically opposite one another on the connector portion 802. Only one of the alignment protrusions 807 is shown in FIG. 8. The alignment protrusions 807 are configured to align the positioning member 120 relative to the handle 108 and/or the activation device 150 when the positioning member 120 is connected to the handle 108. Specifically, in the example embodiment, each of the alignment protrusions 807 is configured to align with one of two alignment recesses 170 (shown in FIG. 3) defined by the body 122 of the handle 108 when the positioning member 120 is connected to the handle 108. The alignment protrusions 807 and the alignment recesses 170 permit two rotational positions of the positioning member 120 relative to the handle 108 when the positioning member 120 is connected to the handle 108. The two rotational positions allow a user of the surgical device 100 to selectively orient the positioning member 120 in one of the two rotational positions to enable selective use of a finger or a thumb to actuate the activation device 150.

In the example embodiment, each of the alignment protrusions 807 is located along a portion of the connecter portion 802 defined by one of two circumferentially extending slots 808 located diametrically opposite one another on the connector portion 802. Only one of the slots 808 is shown in FIG. 8. Each of the slots 808 defines an arm 809 at a proximal end of the connector portion 808. The slots 808 enable deflection of the arms 809 as the positioning member 120 is inserted over the distal end 112 of the handle 108, causing the arms 809 to behave like a spring and bias the alignment protrusions 807 into engagement with the alignment recesses 170.

The leg 804 extends distally from the connector portion 802, and provides a rigid structural connection between the engagement member 806 and the connector portion 802. The leg 804 is sufficiently rigid to inhibit flexing or bending of the positioning member 120 when the engagement member 806 is pressed against a patient's eye and the leg 804 is placed under compression. In the illustrated embodiment, the leg 804 has an arcuate or semi-circular cross-section, although in other embodiments, the leg 804 may have any suitable configuration that enables the positioning member 120 to function as described herein. Further, in the illustrated embodiment, the leg 804 extends only partially around (i.e., in a circumferential direction) the longitudinal axis 102 of the surgical device 100. The leg 804 thereby defines a viewing opening or window that provides direct line-of-sight to the trocar-cannula assembly 114 and the desired incision site. In other embodiments, the leg 804 may extend substantially or entirely around the longitudinal axis 102 of the surgical device 100. In such embodiments, the leg 804 may be constructed of a transparent material to enable line-of-sight to the trocar-cannula assembly 114 and the desired incision site.

The engagement member 806 is disposed at the distal end of the leg 804, and is configured to engage a generally spherical surface, such as the sclera of a patient's eye, to facilitate alignment and positioning of the surgical device 100 during surgical procedures. Specifically, the engagement member 806 includes alignment feet 810 and an engagement surface 812.

As shown in FIG. 8, each alignment foot 810 includes an outer alignment edge 814 that adjoins the engagement surface 812. The alignment edge 814 is shaped complementary to anatomical features of the body to facilitate alignment of the surgical device 100 with a desired incision site. In the illustrated embodiment, the alignment edge 814 is shaped complementary to the corneal limbus of the eye, and has an arcuate shape that is convex with respect to the longitudinal axis 102 of the surgical device 100. In the illustrated embodiment, the alignment edge 814 has a suitable radius of curvature to permit general alignment of the alignment edge 814 with the limbus of the eye. In some embodiments, the alignment edge 814 may have a radius of curvature in a range of 5.0 mm and 7.0 mm, or in a range of 5.4 mm to 6.4 mm. In some embodiments, the alignment edge 814 has a radius of curvature of about 6.0 mm, which corresponds to the radius of curvature of the corneal limbus in an average human adult eye. In other embodiments, the alignment edge 814 may have a radius of curvature less than 5.0 mm, or greater than 7.0 mm (e.g., when used for veterinary procedures).

The alignment edge 814 is spaced radially outward from the central longitudinal axis 102 of the surgical device 100. In the illustrated embodiment, each alignment edge 814 is spaced from the central longitudinal axis 102 of the surgical device 100 by a suitable distance such that, when the alignment edge 814 of one of the alignment feet 810 is aligned with the limbus of the eye, the projected incision site of the trocar-cannula assembly 114 is a predetermined radial distance away from the limbus. The radial spacing between the alignment edges 814 and the longitudinal centerline of the surgical device 100 generally corresponds to the spacing between the limbus and the Pars Plana of the eye. The positioning member 120 of the illustrated embodiment thereby facilities alignment of the trocar-cannula assembly 114 with the Pars Plana of the eye.

The engagement surface 812 is the most distal surface of the surgical device 100, and is disposed for engagement with the tissue or organ to be incised with the surgical device 100. In the illustrated embodiment, the engagement surface 812 is partially defined by the bottom surfaces of the alignment feet 810.

FIG. 9 is a side view of the surgical device 100 with the trocar-cannula assembly 114 and the piston 142 in the extended position (i.e., after the propulsion system 116 has been activated). FIG. 10 is an enlarged cross-sectional view of the surgical device 100 shown in FIG. 9. In FIG. 10, the propulsion system 116 has been activated, and the trocar-cannula assembly 114 is shown as being inserted into a patient's eye, indicated by the dotted line 1002. As shown in FIG. 10, the engagement surface 812 is configured to orient the surgical device 100 (specifically, the trocar 136) at a predetermined oblique entry angle 1004 when the engagement surface 812 is positioned flush with the tissue or organ to be incised with the surgical device 100. The entry angle 1004 may be defined as the angle of incidence between the trocar 136 and the normal or perpendicular line of the surface incised by the trocar 136 at the point of insertion. In the illustrated embodiment, the engagement surface 812 is configured to orient the surgical device 100 at an optimal entry angle for incisions through the sclera of the eye. Specifically, the engagement surface 812 of the illustrated embodiment has a generally spherical contour, complementary to the sclera of an eye. In other words, the engagement surface 812 defines a spherical surface, also indicated by the dotted line 1002, that is sized and shaped complementary to the sclera of an eye. The entry angle 1004 is generally equivalent to the angle between the trocar 136 or the longitudinal axis 102 of the surgical device 100, and the normal or perpendicular line of the spherical surface 1002 defined by the engagement surface 812 that extends through the point at which the trocar 136 or longitudinal axis 102 intersect the spherical surface 1002. In other words, the longitudinal axis 102 of the surgical device 100 intersects the spherical surface 1002 at an intersection point, and defines an oblique entry angle relative to a normal line of the spherical surface 1002 that extends through the intersection point.

The engagement member 806 and the engagement surface 812 are oriented relative to the rest of the surgical device 100 such that, when the engagement surface 812 is positioned flush with the sclera of the eye, the surgical device 100 is oriented at the predetermined entry angle 1004 relative to the point of incision of the trocar 136. In some embodiments, the predetermined entry angle 1004 is between 10° and 60°. In certain embodiments, the predetermined entry angle 1004 is between 20° and 50°, more suitably between 25° and 35°, and even more suitably, about 30°.

In some embodiments, such as the embodiment shown in FIG. 8, the engagement member 806 may be textured or include other gripping features to facilitate gripping the eye (or other organ or tissue) to maintain the position and orientation of the surgical device 100 relative to the eye. In the illustrated embodiment, the engagement member 806 includes laterally-spaced ridges 816 that protrude from the engagement surface 812. The ridges 816 facilitate gripping and reducing slippage between the eye and the engagement member 806 when the engagement surface 812 is positioned flush with the sclera of the eye.

In the illustrated embodiment, the engagement member 806 includes two alignment feet 810, and is symmetrical about the longitudinal axis 102 of the surgical device 100. Each of the alignment feet 810 includes an alignment edge 814 that is shaped complementary to the corneal limbus of the eye, and that has an arcuate shape that is convex with respect to the longitudinal axis 102 of the surgical device 100. The alignment feet 810 are laterally spaced from one another to permit the trocar-cannula assembly 114 to move axially past the alignment feet 810 when the propulsion system 116 is activated.

The configuration of the engagement member 806 and the alignment feet 810 allows the trocar-cannula assembly 114 to be inserted at a desired orientation (e.g., superiorly or temporally) without changing the entry angle of the trocar-cannula assembly 114. In particular, the positioning member 120 may be rotated 180° about the longitudinal axis 102 of the surgical device 100 to change the orientation at which the trocar-cannula assembly 114 is inserted (e.g., superiorly or temporally), without changing the resulting entry angle 1004 of the surgical device 100 relative to the eye. For example, for some surgical procedures, it is desirable for an instrument cannula (e.g., cannula 138) to point towards the surgeon, or away from the patient's nose. That is, it is desirable for the instrument cannula to point superiorly (i.e., with the proximal end of the cannula pointing towards the superior portion of the eye) when the cannula is inserted on the temporal or nasal side of the eye, and to point temporally (i.e., with the proximal end of the cannula pointing towards the temporal portion of the eye) when the cannula is inserted on the superior or inferior side of the eye. Accordingly, a surgeon may select which of the alignment feet 810 to use based upon the desired resulting orientation of the cannula 138 relative to the eye. For example, when forming an incision on the temporal side of an eye, aligning one of the alignment feet 810 with the corneal limbus will result in the trocar-cannula assembly 114 being oriented towards the inferior portion of the eye, while aligning the other of the alignment feet 810 with the corneal limbus will result in the trocar-cannula assembly 114 being oriented towards the superior portion of the eye. The trocar-cannula assembly 114 will be oriented at the same entry angle, regardless of which of the two alignment feet 810 is used.

In the illustrated embodiment, the positioning member 120 is formed separately from the handle 108, and connected to the handle 108 by inserting the connector portion 802 over the distal end of the handle 108 until the retention tabs 126 engage the distal surface of the connector portion 802. In other embodiments, the handle 108 and the positioning member 120 may be formed integrally as a single unit, for example, by injection molding or casting processes.

In use, the surgical device 100 is used to incise a tissue or organ and to insert the cannula 138 in the tissue or organ to provide access into a cavity. In ophthalmic surgical procedures, the surgical device 100 is used to form a sclerotomy at the Pars Plana within a patient's eye, and to insert the cannula 138 through the sclera of the eye to provide access to the posterior chamber of the eye.

In an embodiment, a method of using the surgical device 100 includes aligning the positioning member 120 with one or more anatomical features of the eye, such as the corneal limbus, pressing the engagement surface 812 flush against the sclera of the eye such that the surgical device 100 and the trocar-cannula assembly 114 are oriented at the desired predetermined entry angle 1004, and activating the propulsion system 116 using the activation device 150 to drive the trocar-cannula assembly 114 forward and form an incision through the sclera of the eye with the trocar 136.

In the example embodiment, aligning the positioning member 120 includes aligning at least one of the alignment feet 810 with an anatomical feature of the eye. Specifically, aligning the positioning member 120 includes aligning the alignment edge 814 of one of the alignment feet 810 with the corneal limbus of the eye. As noted above, aligning the alignment edge 814 with the corneal limbus provides a desired radial spacing between the limbus and the trocar insertion point, and facilities insertion of the trocar 136 through the Pars Plana.

When the propulsion system 116 is activated, the trocar-cannula assembly 114 is driven by the propulsion system 116 axially in the forward direction 118 by the stroke length 164. The propulsion system 116 stops forward advancement of the trocar-cannula assembly 114 just prior to the hub 502 of the cannula 138 contacting the sclera to prevent excess force being imparted to the sclera. That is, the propulsion system 116 stops forward movement of the trocar-cannula assembly 114 to prevent the hub 502 of the cannula 138 from moving axially past the engagement surface 812 of the positioning member 120.

In the example embodiment, the propulsion system 116 is activated by depressing the trigger 152 until the latch 162 disengages the lip 708 of the piston 142. When the latch 162 disengages the lip 708 of the piston 142, the compressed helical spring 140 drives the piston 142 axially in the forward direction 118, and the piston 142 drives the trocar-cannula assembly 114 axially in the forward direction 118 by a distance equal to the stroke length 164. As the piston 142 is being driven forward, the trocar 136, followed by the shaft 504 of the cannula 138, enters the sclera via the Pars Plana at the predetermined entry angle 1004 determined by the positioning member 120. As noted above, the propulsion system 116 drives the trocar-cannula assembly 114 with a force and velocity greater than that typically applied by manual manipulation. In some embodiments, the propulsion system 116 moves the trocar-cannula assembly 114 by the stroke length 164 in less than about 0.5 seconds, or even less than about 0.1 seconds. The trocar 136 and cannula 138 are moving quickly enough that the inertia of the eye tissue is not overcome to a significant degree by the force generated during the creation of the incision and subsequent insertion of the cannula 138.

At the end of the piston stroke, the distal face of the cannula hub 502 is stopped just short of making contact with the sclera to prevent excess force being imparted to the sclera. In the illustrated embodiment, the stop pin 166 prevents forward axial travel of the piston 142 and the trocar-cannula assembly 114 beyond the stroke length 164 by engaging inner surfaces of the piston 142 along the elongate slot 714. Once the trocar 136 and cannula 138 have stopped, the surgeon removes the cannula 138 by sliding the cannula 138 along the trocar 136, and removing the trocar 136 from the surgical site.

In some embodiments, the surgical device 100 is a single use device, and is not intended to be reloaded or reused. In other embodiments, the surgical device 100 is configured for multiple uses, and may be sterilized and reloaded with another cannula after a first cannula is inserted into a surgical site. For example, after a first cannula is inserted into a surgical site, a second cannula may be inserted over the cutting tip 406 of the trocar 136, and moved axially along the trocar 136 to a desired position along the trocar 136. The propulsion system 116 may be "reloaded" by pushing the piston 142 axially backward into the cavity 130 of the handle 108 until the lip 708 of the piston 142 passes the latch 162 of the trigger 152. When the lip 708 of the piston 142 passes the latch 162, the trigger spring 154 moves the trigger 152 radial outward to the first, undepressed position (shown in FIG. 2), and the latch 162 engages the lip 708 of the piston 142, thereby inhibiting forward axial movement of the piston 142. In this state, the surgical device 100 is ready for use.

In some embodiments, the surgical device 100 is designed to facilitate removal of the cannula 138 from the trocar 136 without the use of additional instruments and/or user interaction. In some embodiments, for example, the surgical device 100 includes a cannula removal device that removes the cannula 138 from the trocar 136 after the propulsion system 116 is activated. Additionally or alternatively, the surgical device 100 may be configured to automatically retract the trocar 136 from the extended position (shown in FIGS. 9 and 10) to a retracted position after the propulsion system 116 is activated to facilitate removal of the cannula 138 from the trocar 136.

Figure 11:
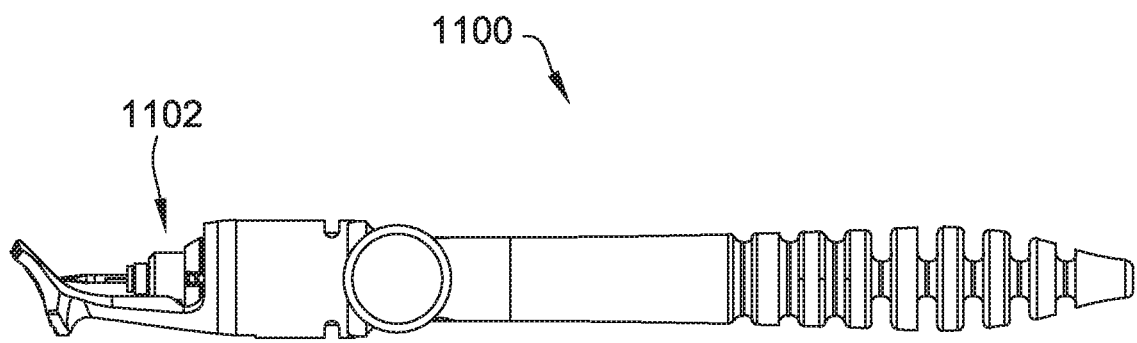
FIG. 11 is a side view of an example surgical device that includes a cannula removal device.
Figure 12:
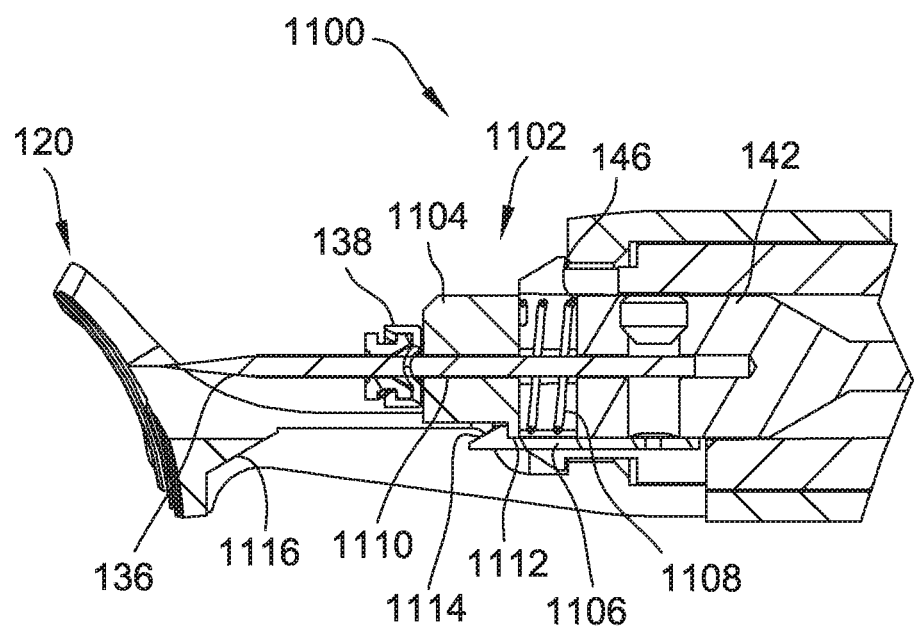
FIG. 12 is an enlarged sectional view of the distal end of the surgical device shown in FIG. 11.

FIG. 11 is a side view of an example surgical device 1100 that includes a cannula removal device 1102, and FIG. 12 is an enlarged sectional view of the distal end of the surgical device 1100. Unless otherwise noted, the surgical device 1100 has the same configuration and functions in the same manner as the surgical device 100 described above with reference to FIGS. 1-10. As such, like reference characters are used to identify components of the surgical device 1100 that are the same as components of the surgical device 100.

As shown in FIG. 12, the cannula removal device 1102 includes a sleeve or collar 1104 connected to the piston 142 of the propulsion system by a latch 1106, and a spring 1108 (broadly, a biasing element) disposed between the collar 1104 and the piston 142.

The collar 1104 defines a central opening 1110 sized and shaped to receive the trocar 136 therein such that the collar 1104 may be positioned on the trocar 136. The opening 1110 has a sufficiently large diameter to enable the trocar 136 to move or slide freely through the opening, thereby enabling the collar 1104 to freely slide along the trocar 136. As shown in FIG. 12, the collar 1104 is positioned adjacent the cannula 138 on the trocar 136, and abuts a proximal end of the cannula 138. Moreover, the collar 1104 is positioned between the cannula 138 and the piston 142, and in engagement with the cannula 138 so as to drive the cannula 138 forward when the propulsion system is activated. The collar 1104 also includes a protrusion 1112 extending radially outward from the collar 1104 for engaging the latch 1106.

The latch 1106 is connected to the piston 142, and extends distally past the distal end 146 of the piston 142 a sufficient distance to engage the protrusion 1112 on the collar 1104. In some embodiments, the latch 1106 is formed separately from and connected to the piston 142 by suitable connection means, including, for example and without limitation, adhesives, screws, and/or pins. In other embodiments, the latch 1106 is formed integrally with the piston 142, for example, by a suitable molding process (e.g., injection molding).

As shown in FIG. 12, the latch 1106 includes a tapered distal surface 1114 that is positioned in axially alignment with a complementary tapered proximal surface 1116 of the positioning member 120. The latch has a generally flexible construction, and is configured to deflect radially outward when the tapered distal surface 1114 engages the tapered proximal surface 1116 of the positioning member 120 upon activation of the propulsion system. The latch 1106 is configured to deflect radially outward a sufficient distance to disengage the collar protrusion 1112.

The spring 1108 biases the collar 1104 away from the piston 142, and into engagement with the latch 1106 and/or the cannula 138 when the piston 142 is in the first, retracted position (shown in FIGS. 11 and 12). When the latch 1106 disengages the collar 1104, the spring 1108 biases the collar 1104 into engagement with the cannula 138. Additionally, the counter-force of the spring 1108 biases the piston 142 and the trocar 136 in the rearward direction, and causes the piston 142 and the trocar 136 to retract in the rearward direction following activation of the propulsion system, as described in more detail herein. In the example embodiment, the spring 1108 is a helical spring. In other embodiments, the spring 1108 may be any suitable biasing element that enables the surgical device 1100 to function as described herein.

In some embodiments, the spring 1108 has a suitable construction (e.g., spring constant) to retract the trocar 136—i.e., displace the trocar 136 in the rearward direction—at a similar velocity as the propulsion system. In some embodiments, for example, the spring 1108 is configured to retract the trocar 136 at a velocity between 0.05 m/s and 1 m/s, or between 0.1 m/s and 1 m/s. In other embodiments, the spring 1108 may be configured to retract the trocar at a velocity less than 0.05 m/s, or at a velocity greater than 1 m/s.

Figure 13:
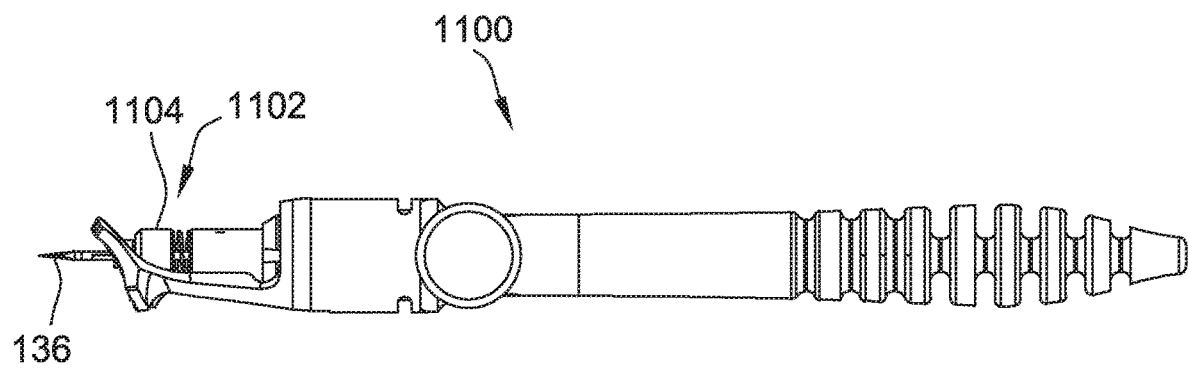
FIG. 13 is another side view of the surgical device shown in FIG. 11, showing an instantaneous position of a trocar and a collar of the surgical device following activation of the propulsion system.
Figure 14:
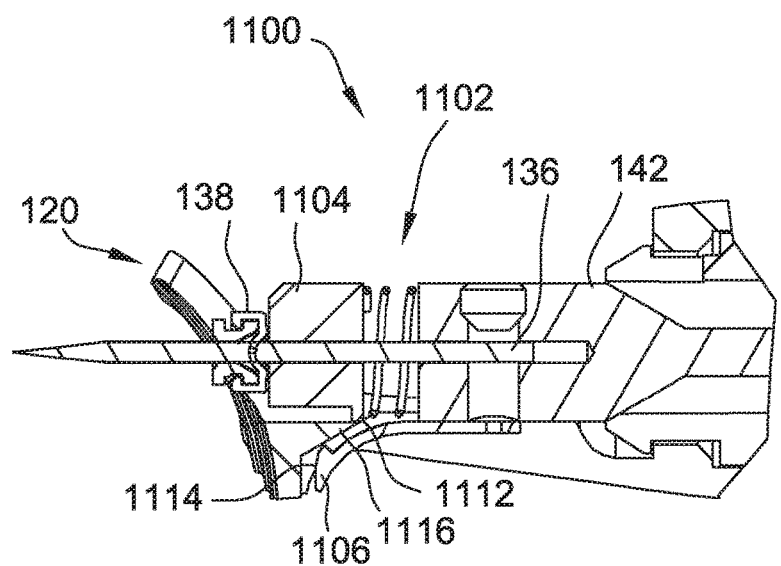
FIG. 14 is an enlarged sectional view of the distal end of the surgical device shown in FIG. 13.
Figure 15:
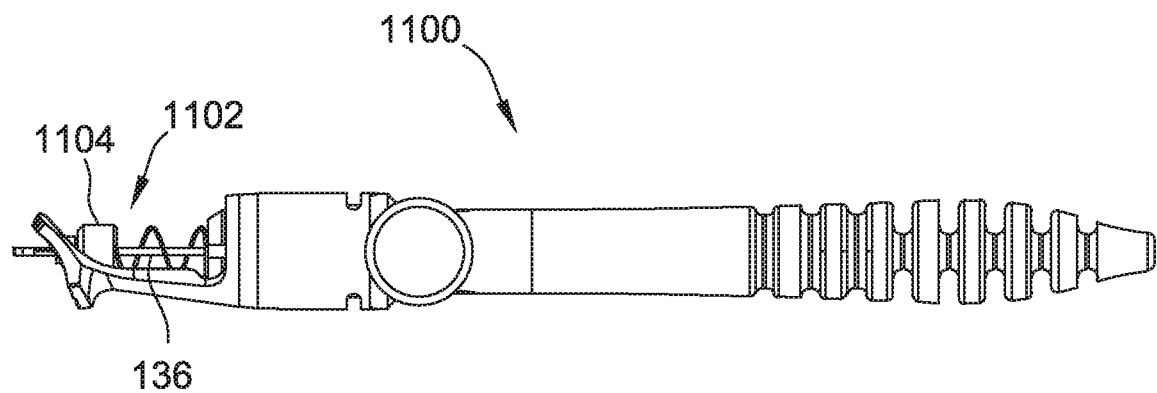
FIG. 15 is another side view of the surgical device shown in FIG. 11, showing the trocar in a retracted position following activation of the propulsion system.

FIG. 13 is another side view of the surgical device 1100 showing an instantaneous position of the trocar 136 and the collar 1104 following activation of the propulsion system, and FIG. 14 is an enlarged sectional view of the distal end of the surgical device 1100 shown in FIG. 13. FIG. 15 is another side view of the surgical device 1100 showing the trocar 136 in a retracted position following activation of the propulsion system, and FIG. 16 is an enlarged sectional view of the distal end of the surgical device 1100 shown in FIG. 15.

In use, the surgical device 1100 operates in substantially the same manner as the surgical device 100 described above with reference to FIGS. 1-10, except in the surgical device 1100, the cannula 138 can be removed from the trocar 136 without additional instruments and/or user interaction, and the trocar 136 automatically retracts following activation of the propulsion system. More specifically, as shown in FIGS. 13 and 14, when the propulsion system is activated, the propulsion system drives the piston 142 axially in the forward direction, and the piston 142 drives the trocar 136, the cannula 138, and the collar 1104 axially in the forward direction. As the piston 142 is driven in the forward direction, the tapered distal surface 1114 of the latch 1106 engages the tapered proximal surface 1116 of the positioning member 120, causing the latch 1106 to deflect radially outward. Continued forward movement of the piston 142 and the latch 1106 causes the latch 1106 to deflect further radially outward until the latch 1106 disengages the collar protrusion 1112.

Figure 16:
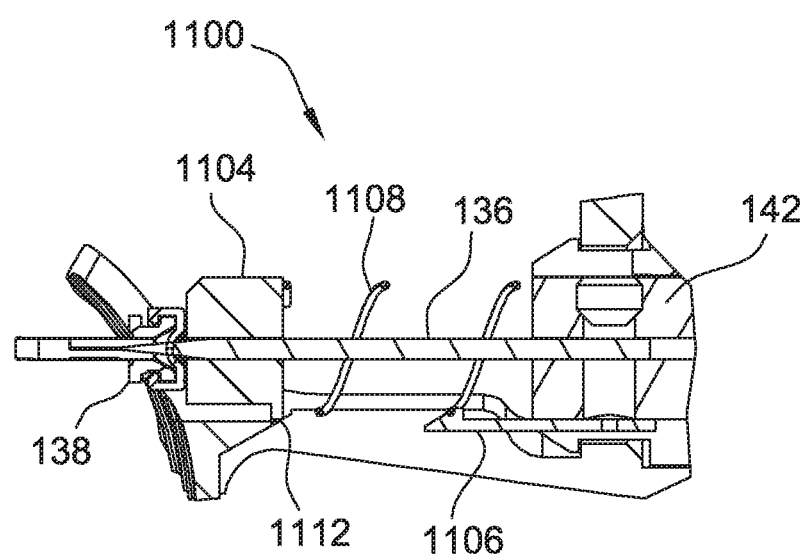
FIG. 16 is an enlarged sectional view of the distal end of the surgical device shown in FIG. 15.

As shown in FIGS. 15 and 16, when the latch 1106 disengages the collar protrusion 1112, the spring 1108 forces the piston 142 and collar 1104 away from one another, causing the trocar 136 to retract out of the collar 1104 in the rearward direction. Moreover, the biasing force of the spring 1108 biases the collar 1104 against the cannula 138, enabling the trocar 136 to be removed from the cannula 138 without additional instrumentation or user interaction. Thus, the cannula removal device 1102 removes the cannula 138 from the trocar 136, and causes the trocar 136 to automatically retract. Accordingly, the cannula removal device 1102 may also be referred to herein as a trocar retraction mechanism.

In some embodiments, the collar 1104 may also function as a sharps shield by covering the cutting tip 406 (shown in FIG. 4) of the trocar 136 after the trocar 136 is retracted by the trocar retraction mechanism.

As described above, the surgical device 1100 enables the cannula 138 to be removed from the trocar 136 without the use of additional instruments and/or user interaction. Additionally, the surgical device 1100 automatically retracts the trocar 136 from the extended position (shown in FIGS. 13 and 14) to a retracted position (shown in FIGS. 15 and 16) after the propulsion system is activated. Thus, the surgical device 1100 enables the entire cannula insertion procedure to be carried out with a single hand. That is, the surgical device 1100 makes the cannula insertion procedure a one- or single-handed operation, enabling the surgeon to use their other hand for other operations.

In some embodiments, surgical devices of the present application may be configured to insert multiple cannulas during a surgical procedure. In some embodiments, for example, multiple cannulas may be loaded onto a single trocar, with the most distal cannula being positioned for insertion into a tissue or organ. Following the insertion of one of the cannulas, the next most distal cannula may be repositioned for insertion into a tissue or organ.

In other embodiments, surgical devices of the present application may include a plurality of propulsion systems, such as the propulsion system 116 described above with reference to FIGS. 1-10, where each of the propulsion systems is operatively connected to a corresponding trocar-cannula assembly and is operable to drive the corresponding trocar-cannula assembly axially in a forward direction.

Figure 17:
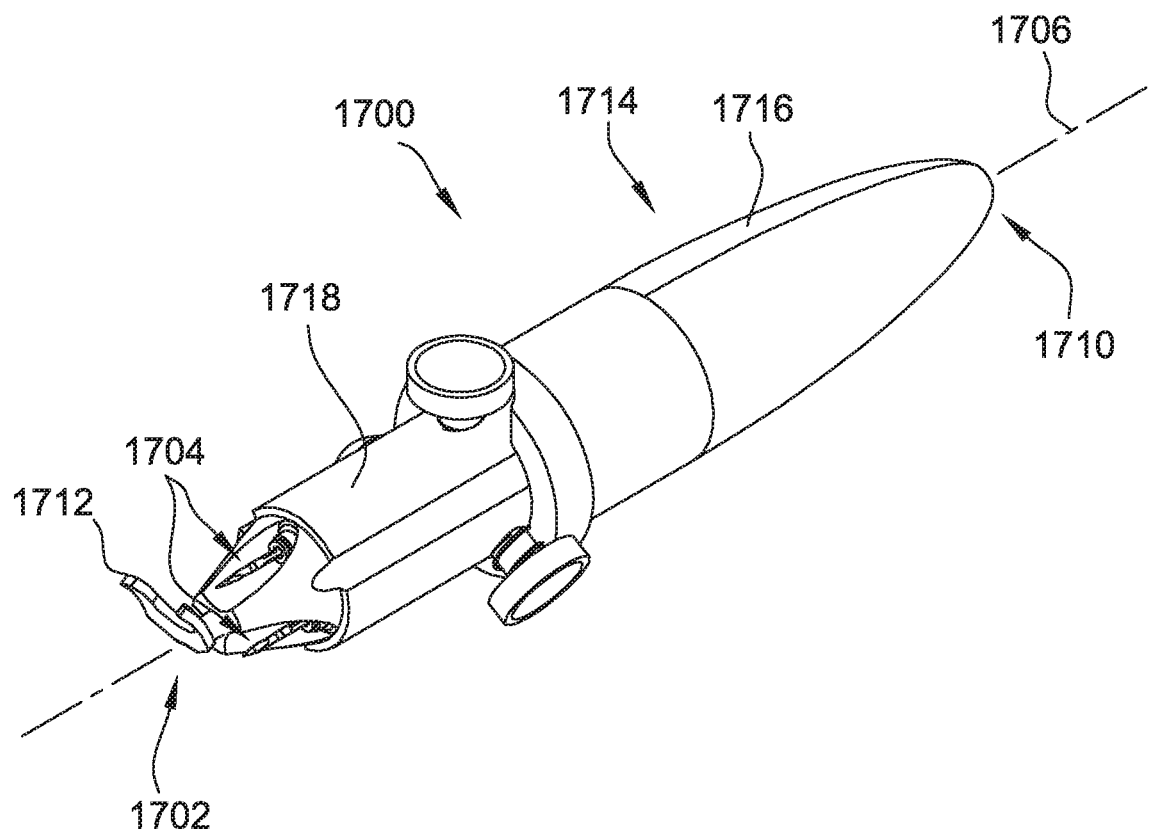
FIG. 17 is a perspective view of an example surgical device configured to insert multiple cannulas during a surgical procedure.
Figure 18:
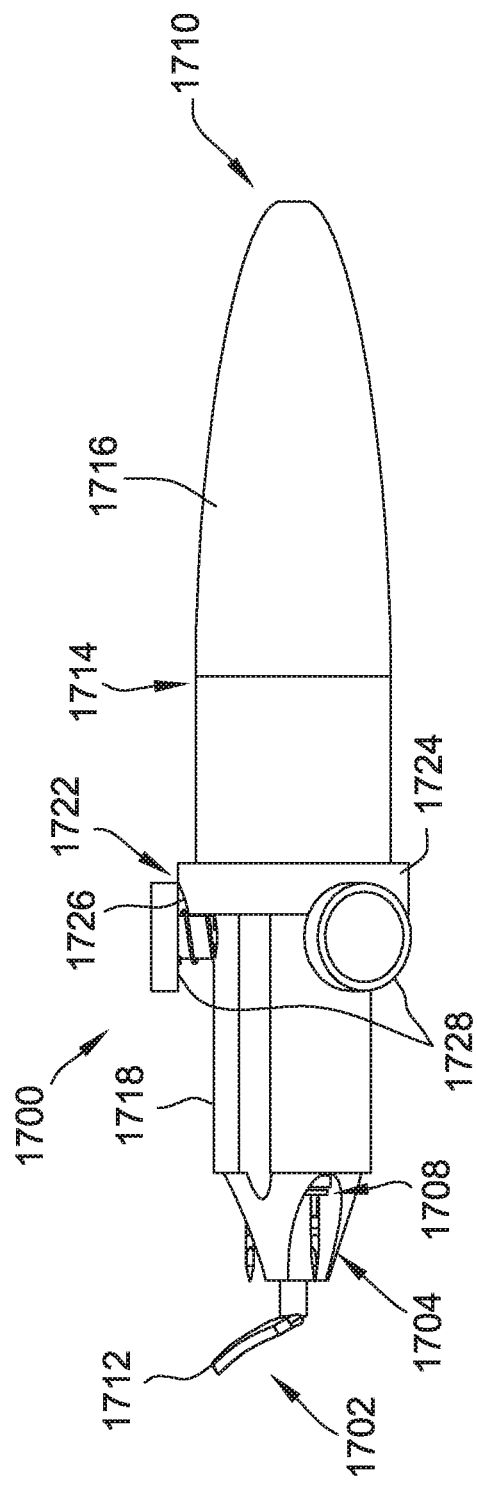
FIG. 18 is a side view of the surgical device shown in FIG. 17.
Figure 19:
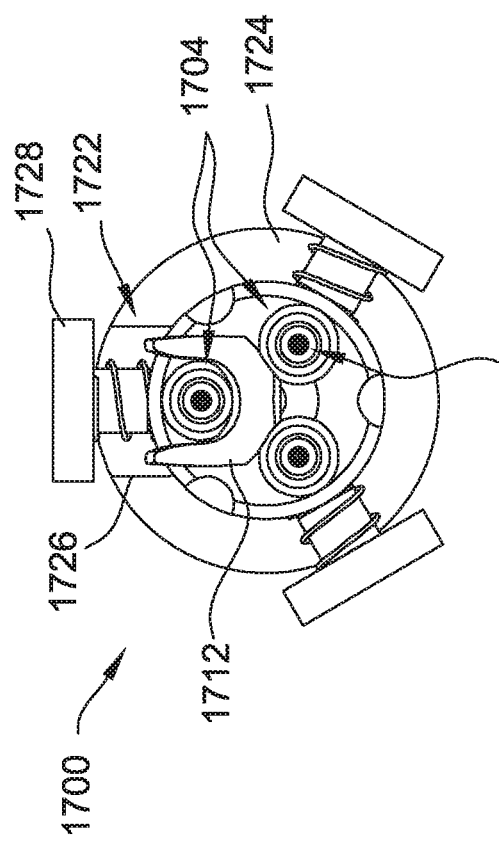
FIG. 19 is an end view of a distal end of the surgical device shown in FIG. 17.

FIG. 17 is a perspective view of an example surgical device 1700 configured to insert multiple cannulas during a surgical procedure. FIG. 18 is a side view of the surgical device 1700, and FIG. 19 is an end view of a distal end 1702 of the surgical device 1700. As shown in FIGS. 17-19, the surgical device 1700 includes a plurality of propulsion systems 1704 arranged circumferentially about a central longitudinal axis 1706 of the surgical device 1700. Each of the propulsion systems 1704 is operatively connected to a corresponding trocar-cannula assembly 1708, and is operable to drive the corresponding trocar-cannula assembly 1708 axially in a forward direction away from a proximal end 1710 of the surgical device 1700. The example embodiment includes three propulsion systems 1704 arranged circumferentially at about 120° intervals about the central longitudinal axis 1706. Other embodiments may include more than or less than three propulsion systems.

In the example embodiment, each of the trocar-cannula assemblies 1708 is identical to the trocar-cannula assembly 114 described above with reference to FIGS. 1-10. For example, each of the trocar-cannula assemblies 1708 includes a trocar 136 and a cannula 138 (both shown in FIG. 4) releasably mounted on the trocar 136. In other embodiments, the trocar-cannula assemblies 1708 may have a construction or configuration different than the trocar-cannula assembly 114.

Further, in the example embodiment, each of the propulsion systems 1704 has substantially the same configuration and operates in substantially the same manner as the propulsion system 116 described above with reference to FIGS. 1-10. In other embodiments, the propulsion systems 1704 may have any suitable configuration that enables the surgical device 1700 to function as described herein.

The surgical device 1700 also includes a positioning member 1712 disposed at the distal end 1702 of the surgical device 1700. The positioning member 1712 is substantially identical to, and operates in substantially the same manner as the positioning member 120 described above with reference to FIGS. 1-10. The plurality of propulsion systems 1704 is rotatable relative to the positioning member 1712 such that each of the propulsion systems 1704 is selectively alignable with the positioning member 1712. That is, each of the propulsion systems 1704 is selectively positionable in axial alignment with the positioning member 1712. In the example embodiment, the plurality of propulsion systems 1704 is rotatable about the surgical device central longitudinal axis 1706, although in other embodiments, the plurality of propulsion systems 1704 may be rotatable about another axis that allows each of the propulsion systems to be selectively aligned with the positioning member 1712.

In the example embodiment, the surgical device 1700 includes a multiple-piece housing 1714 that includes a plurality of sections that rotate relative to one another. More specifically, in the example embodiment, the housing 1714 includes a proximal section 1716 and a distal section 1718. The proximal section 1716 defines a handle of the surgical device 1700, and the distal section 1718 houses or encloses the plurality of propulsion systems 1704. The proximal section 1716 is connected to the positioning member 1712 such that the proximal section 1716 and the positioning member 1712 are operable to rotate together, as a unit, relative to the distal section 1718. In other words, the proximal section 1716 is rotatably fixed to the positioning member 1712. Each of the propulsion systems 1704 are secured to the distal section 1718 of the housing 1714 such that rotation of the distal section 1718 causes the plurality of propulsion systems 1704 to rotate about the central longitudinal axis 1706.

The configuration of the housing 1714 facilitates selective alignment of the propulsion systems 1704 with the positioning member 1712 by providing various points at which a user can grasp the surgical device 1700 while rotating other portions of the surgical device 1700. For example, a user of the surgical device 1700 can grasp the surgical device 1700 along the housing proximal section 1716, and rotate the housing distal section 1718 to selectively align one of the propulsion systems 1704 with the positioning member 1712. Alternatively, a user can grasp the distal section 1718 with one hand, and rotate the housing proximal section 1716 with the other hand to rotate and selectively align the positioning member 1712 with one of the propulsion systems 1704.

In the example embodiment, the surgical device 1700 also includes an alignment feature 1722 that enables activation of only the propulsion system 1704 aligned with the positioning member 1712. That is, the alignment feature 1722 prevents activation of propulsion systems 1704 that are not aligned with the positioning member 1712. In the example embodiment, the alignment feature 1722 includes an annular lip or rim 1724 that extends radially outward from the housing 1714 (specifically, the proximal section 1716 of the housing 1714), and an arcuate cutout 1726 defined in the rim 1724. The cutout 1726 is shaped complementary to an activation device or trigger 1728 associated with each of the propulsion systems 1704 such that the trigger 1728 may only be depressed when positioned in radially alignment (i.e., radially aligned) with the cutout 1726.

In use, the surgical device 1700 is used to incise a tissue or organ and to insert multiple cannulas in the tissue or organ to provide access into a cavity. In one embodiment, a method of using the surgical device 1700 includes orienting the surgical device 1700 at a predetermined entry angle at a first incision site using the positioning member 1712, activating a first of the propulsion systems 1704 that is axially aligned with the positioning member 1712 to insert a cannula from the corresponding trocar-cannula assembly 1708 at the first incision site, aligning a second propulsion system 1704 with the positioning member 1712, orienting the surgical device 1700 at a predetermined entry angle at a second incision site using the positioning member 1712, and activating the second propulsion system 1704 to insert a cannula from the corresponding trocar-cannula assembly 1708 at the second incision site. This process may be repeated for each of the propulsion systems 1704 within the surgical device 1700.

The surgical device 1700 may be oriented at the predetermined entry angle using the positioning member 1712 in the same manner described above with references to FIGS. 1-10. In some embodiments, activating the propulsion systems 1704 includes pressing (or depressing) the trigger 1728 associated with the propulsion system 1704. The alignment feature 1722 allows the trigger 1728 to be depressed a sufficient distance to enable activation of the corresponding propulsion system 1704. When the propulsion system 1704 is activated, the corresponding trocar-cannula assembly 1708 is driven axially forward to form an incision through a tissue or organ. The cannula of the trocar-cannula assembly 1708 may then be removed from the trocar, either manually or automatically (e.g., using a cannula removal device). After the cannula is inserted in the tissue or organ, and the trocar removed from the cannula, another one of the propulsion systems 1704 is rotated into alignment with the positioning member 1712, and the process repeated until a desired number of cannulas have been inserted into the tissue or organ, or until all cannulas of the surgical device 1700 have been inserted.

Figure 20:
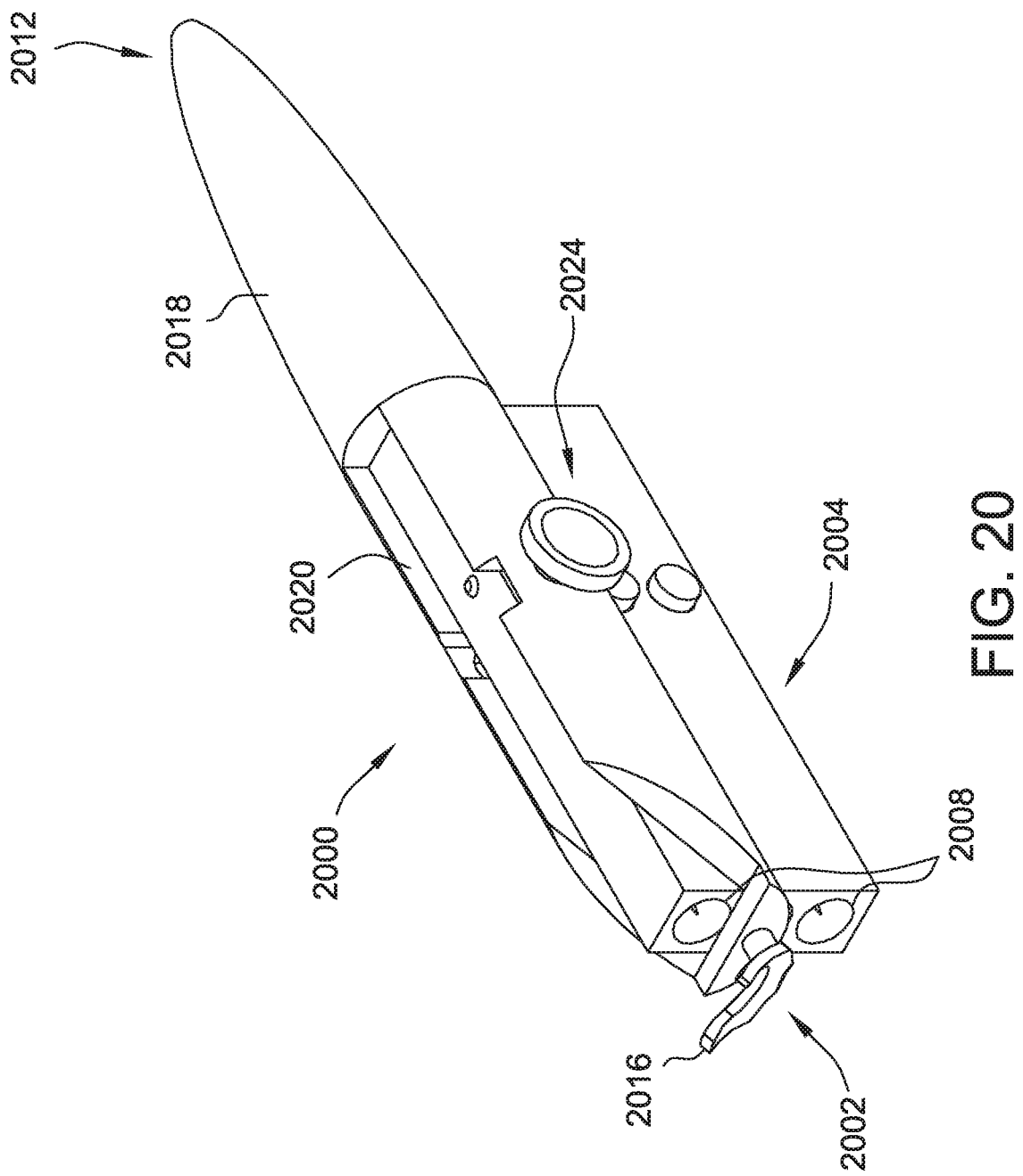
FIG. 20 is a perspective view of another embodiment of a surgical device configured to insert multiple cannulas during a surgical procedure.
Figure 21:
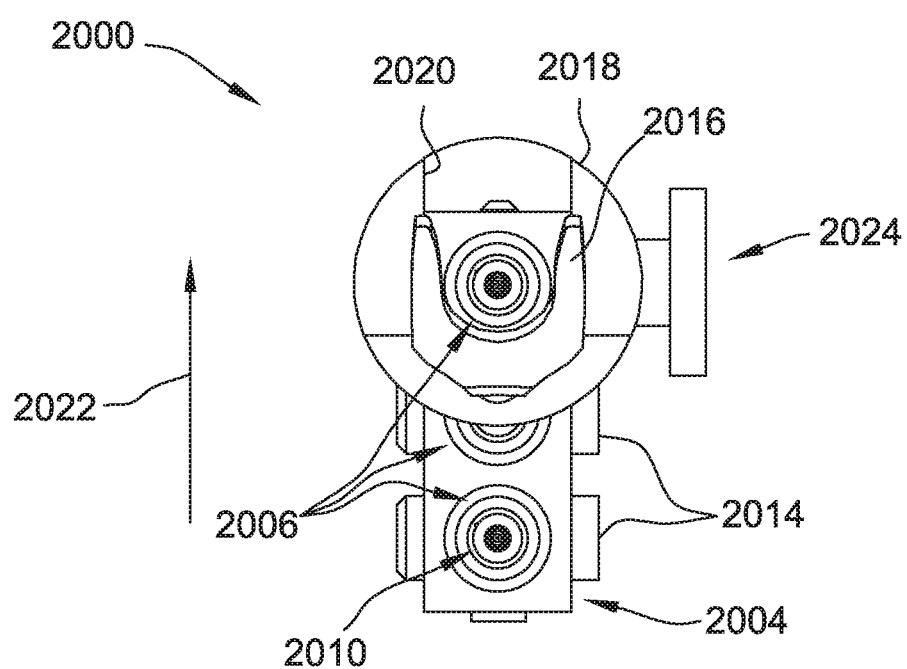
FIG. 21 is an end view of a distal end of the surgical device shown in FIG. 20.

FIG. 20 is a perspective view of another embodiment of a surgical device 2000 configured to insert multiple cannulas during a surgical procedure. FIG. 21 is an end view of a distal end 2002 of the surgical device 2000. As shown in FIGS. 20 and 21, the surgical device 2000 includes a magazine or clip 2004 that holds a plurality of propulsion systems 2006. More specifically, the clip 2004 defines a plurality of chambers 2008, and each of the propulsion systems 2006 is disposed within a corresponding chamber 2008. Each of the propulsion systems 2006 is operatively connected to a corresponding trocar-cannula assembly 2010, and is operable to drive the corresponding trocar-cannula assembly 2010 axially in a forward direction away from a proximal end 2012 of the surgical device 2000. The example embodiment includes three propulsion systems 2006, each disposed within one of three separate chambers 2008. Other embodiments may include more than or less than three propulsion systems.

In the example embodiment, each of the trocar-cannula assemblies 2010 is identical to the trocar-cannula assembly 114 described above with reference to FIGS. 1-10. For example, each of the trocar-cannula assemblies 2010 includes a trocar 136 and a cannula 138 (both shown in FIG. 4) releasably mounted on the trocar 136. In other embodiments, the trocar-cannula assemblies 2010 may have a construction or configuration different than the trocar-cannula assembly 114.

Further, in the example embodiment, each of the propulsion systems 2006 has substantially the same configuration and operates in substantially the same manner as the propulsion system 116 described above with reference to FIGS. 1-10. Further, in the example embodiment, each of the propulsion systems 2006 includes a shaft 2014, similar to the shaft 158 (shown in FIG. 3), that extends through the clip 2004 and outwardly from laterally opposing side of the clip 2004. The shaft 2014 is configured to cooperate with an activation device or trigger of the surgical device 2000, described in more detail below, to activate the corresponding propulsion system 2006. In other embodiments, the propulsion systems 2006 may have any suitable configuration that enables the surgical device 2000 to function as described herein.

The surgical device 2000 also includes a positioning member 2016 disposed at the distal end 2002 of the surgical device 2000. The positioning member 2016 is substantially identical to, and operates in substantially the same manner as the positioning member 120 described above with reference to FIGS. 1-10.

The surgical device 2000 also includes a housing or handle 2018 that defines a slot 2020 extending transversely (i.e., radially) through the handle 2018. The slot 2020 is sized and shaped to receive the clip 2004 therein such that the clip 2004 can be advanced through the slot 2020 in the transverse direction, indicated by arrow 2022 in FIG. 21. Advancement of the clip 2004 through the slot 2020 enables each of the propulsion systems 2006 to be selectively aligned with (i.e., positioned in axially alignment with) the positioning member 2016.

In the example embodiment, the surgical device 2000 also includes a single activation device or trigger 2024 that activates each of the propulsion systems 2006. More specifically, the trigger 2024 is connected to the handle 2018 adjacent the slot 2020, and is depressible in a radial direction into the slot 2020 a sufficient distance to engage one of the shafts 2014 associated with a propulsion system 2006 positioned within the slot 2020. Advancement of the clip 2004 through the slot 2020 enables each of the propulsion systems 2006 to be selectively aligned with the trigger 2024.

Depression of the trigger 2024, and displacement of the shaft 2014 in the radial direction, activates the propulsion system 2006 associated with the shaft 2014.

In use, the surgical device 2000 is used to incise a tissue or organ and to insert multiple cannulas in the tissue or organ to provide access into a cavity. In one embodiment, a method of using the surgical device 2000 includes orienting the surgical device 2000 at a predetermined entry angle at a first incision site using the positioning member 2016, activating a first of the propulsion systems 2006 that is axially aligned with the positioning member 2016 to insert a cannula from the corresponding trocar-cannula assembly 2010 at the first incision site, aligning a second of the propulsion systems 2006 with the positioning member 2016, orienting the surgical device 2000 at a predetermined entry angle at a second incision site using the positioning member 2016, and activating the second of the propulsion systems 2006 to insert a cannula from the corresponding trocar-cannula assembly 2010 at the second incision site. This process may be repeated for each of the propulsion systems 2006 within the surgical device 2000.

The surgical device 2000 may be oriented at the predetermined entry angle using the positioning member 2016 in the same manner described above with reference to FIGS. 1-10. In some embodiments, activating the propulsion systems 2006 includes advancing the clip 2004 in the transverse direction 2022 to position one of the propulsion systems within the slot 2020, and pressing (or depressing) the trigger 2024 into engagement with the shaft 2014 of the corresponding propulsion system 2006. Displacement of the shaft 2014 activates the corresponding propulsion system 2006, which drives or propels the corresponding trocar-cannula assembly 2010 axially forward to form an incision through a tissue or organ. The cannula of the trocar-cannula assembly 2010 may then be removed from the trocar, either manually or automatically (e.g., using a cannula removal device). After the cannula is inserted in the tissue or organ, and the trocar removed from the cannula, the clip 2004 is advanced further into the slot 2020 until another one of the propulsion systems 2006 is positioned in alignment with the positioning member 2016, and the process repeated until a desired number of cannulas have been inserted into the tissue or organ, or until all cannulas of the surgical device 2000 have been inserted.

Example embodiments of surgical devices are described above in detail. The surgical devices are not limited to the specific embodiments described herein, but rather, components of the surgical devices may be used independently and separately from other components described herein. Additionally, features described with reference to one embodiment may be implemented in other embodiments of the surgical devices. For example, features described with reference to the surgical device 100 may be implemented in any of the surgical devices 1100, 1700, and 2000, and vice versa.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A surgical device comprising:
   a trocar;
   a cannula releasably mounted on the trocar, the cannula including a hub and having a central opening through which the trocar extends;
   a propulsion system connected to the trocar and operable to drive the trocar axially in a forward direction away from a proximal end of the surgical device;
   a latch; and
   a collar connected to the propulsion system by the latch and operable to remove the cannula from the trocar after the propulsion system is activated, wherein the latch disengages the collar following activation of the propulsion system.

2. The surgical device as set forth in claim 1, wherein the surgical device further includes a positioning member disposed at a distal end of the surgical device, the positioning member including a tapered proximal surface configured to engage the latch and cause the latch to deflect radially outward when the propulsion system is activated.

3. The surgical device as set forth in claim 2, wherein the latch includes a tapered distal surface that is positioned in axial alignment with the tapered proximal surface of the positioning member.

4. The surgical device as set forth in claim 1, wherein the collar is connected to the propulsion system by a spring that biases the collar away from the propulsion system and into engagement with the cannula.

5. The surgical device as set forth in claim 4, wherein the spring biases the trocar in a rearward direction, and wherein the spring is configured to cause the trocar to automatically retract after the propulsion system is activated.

6. The surgical device as set forth in claim 5, wherein the collar covers a cutting tip of the trocar after the trocar is retracted.

7. The surgical device as set forth in claim 1, wherein the collar is positioned on the trocar adjacent a proximal end of the cannula.

8. The surgical device as set forth in claim 1, wherein the collar defines an opening sized to receive the trocar therein, wherein the trocar is freely movable through the opening.

9. The surgical device as set forth in claim 1, wherein the propulsion system includes a piston moveable between a first, retracted position and a second, extended position upon activation of the propulsion system, wherein the trocar is fixed to the piston.

10. The surgical device as set forth in claim 9, wherein the latch is connected to the piston, and wherein the latch extends distally past a distal end of the piston to engage the collar.

11. The surgical device as set forth in claim 1 further comprising an activation device operatively connected to the propulsion system and operable to activate the propulsion system in response to a user input.

12. The surgical device as set forth in claim 11, wherein the activation device includes a trigger extending radially outward from a handle of the surgical device.

13. The surgical device as set forth in claim 1, wherein the collar comprises a protrusion, and wherein the latch engages the collar via the protrusion.

14. The surgical device as set forth in claim 1, wherein the latch has a flexible construction and is configured to deflect radially outward to disengage the latch.

15. The surgical device as set forth in claim 1, wherein the propulsion system includes a first spring that drives the trocar in the forward direction upon activation of the propulsion system, and wherein the surgical device includes a second spring disposed between the collar and the propulsion system, wherein the second spring causes the trocar to automatically retract after the propulsion system is activated.

16. The surgical device as set forth in claim 15, wherein the second spring is configured to retract the trocar at a velocity of between 0.1 m/s and 1.0 m/s.

17. The surgical device as set forth in claim 1, wherein the trocar has an outer diameter less than or equal to 23-gauge.

18. The surgical device as set forth in claim 1, wherein the propulsion system is configured to displace the trocar by a stroke length from an initial position to a second, fully extended position in less than 0.5 seconds.

19. The surgical device as set forth in claim 1, wherein the surgical device is configured for multiple uses.

20. The surgical device as set forth in claim 1, wherein the collar is connected to the propulsion system by a spring that biases the collar away from the propulsion system and into engagement with the latch.

* * * * *